United States Patent [19]
LaClair

[11] Patent Number: 6,140,041
[45] Date of Patent: Oct. 31, 2000

[54] FLUORESCENT DYE

[75] Inventor: James J. LaClair, San Diego, Calif.

[73] Assignee: The Scripps Research Institute, La Jolla, Calif.

[21] Appl. No.: 09/232,356

[22] Filed: Jan. 15, 1999

Related U.S. Application Data

[63] Continuation-in-part of application No. 09/017,518, Feb. 2, 1998.

[51] Int. Cl.[7] .............................. C12Q 1/00; C12Q 1/68; C12Q 1/54; C12Q 1/37
[52] U.S. Cl. ................................. 435/4; 435/968; 435/6; 435/7.72; 435/7.8; 435/14; 435/23; 435/24; 536/17.3; 536/17.2
[58] Field of Search ................................. 435/4, 968, 6, 435/7.72, 7.8, 14, 23, 24; 536/17.3, 17.2

[56] References Cited

U.S. PATENT DOCUMENTS

| | | | |
|---|---|---|---|
| 4,140,529 | 2/1979 | Pai et al. | 435/4 |
| 4,265,900 | 5/1981 | Stolka et al. | 435/4 |
| 5,179,457 | 1/1993 | Buchwalter et al. | 435/4 |

OTHER PUBLICATIONS

Shin, et al., Solvatochromatic Behavior of Intramolecular Charge–Transfer Diphenylpolyenes in Homogenous Solution and Microheterogenous *J. Phys. Chem. 92*: 2945–2956 (1988).
Akiyama, et al., "Direct C≧C Triple Bond Formation from the C=C Double Bond Hydroxylation into the o–Position of a Nitro Group on the Benzene Nucleus with Potassium t–Butoxide in N,N–Dimethylformamide in the Air", *Bull. Chem. Soc. Jpn. 68*: 2043–2051 (1995).
Roy, et al., "Stereospecific Synthesis of Aryl β–D–N–Acetylglucopyranosides by Phase Transfer Catalysis", *Syn. Comm. 20*: 2097–2102 (1990).
Eigen, et al., "Sorting single molecules: Application to diagnostics and evolutionary biotechnology", *Proc. Natl. Acad. Sci USA 91*: 5740–5747 (1994).
Reichardt, "Solvatochromic Dyes as Solvent Polarity Indicators", *Chem. Rev. 94*: 2319–2358 (1994).
Nie, et al., "Probing Individual Molecules with Confocal Fluorescence Microscopy", *Science 266*: 1018–1021 (1994).
Rigler, "Fluorescence correlations, single molecule detection and large number screening Applications in biotechnology", *J. Biotech. 41*: 177–186 (1995).
Goodwin, et al., "Single–Molecular Detection in Liquids by Laser–Induced Fluorescence", *Acc. Chem. Res. 29*: 607–613 (1996).
Schmidt, et al., "Imaging of single molecule diffusions", *Proc. Natl. Acad. Sci. USA 93*: 2926–2929 (1996).
Edman, et al., "Conformational transitions monitored for single molecules in solution", Proc. Natl. Acad. Sci. USA 93:6710–6715 (1996).
LaClair, "Analysis of highly disfavored processes through pathway–specific correlated fluorescence", *Proc. Natl. Acad. Sci. USA 94*: 1623–1628 (1997).
La Clair, "Selective Detection of the Carbohydrate–Bound State of Concanvalin A at the Single Molecule Level", *J. Am. Chem. Soc. 119*: 7676–7684 (1997).

*Primary Examiner*—Louise N. Leary
*Attorney, Agent, or Firm*—Donald G. Lewis

[57] ABSTRACT

Fluorescent dyes possess reactive linkers for conjugating to nucleic acids, carbohydrates and peptides. The conjugates fluoresce in the visible and UV spectrum and have an excellent solvochromatic response as compared to other fluorescence or chromatic labels. The conjugates are stable but also have medium sensitive. The fluorescent dyes have little triplet state formation and are not photoreactive, making them an excellent substance for biological investigations. Uses for the dyes include protein labeling, DNA labeling, single molecule spectroscopy and fluorescence. A synthesis of the dyes is disclosed. Methods of use include the detection of carbohydrate-protein interactions.

26 Claims, 16 Drawing Sheets

Assignment through analysis of:

locked-conjugated locked-orthogonally

NND

⤴ indicates bonds with rotational freedom

3

4

| solvent | $E_t$ | β-glucoside 1 | | β-maltoside 2 | | β-glucoside 1 | | β-maltoside 2 | |
|---|---|---|---|---|---|---|---|---|---|
| | | $\lambda_A$(max), nm | $\epsilon$, $10^4 cm^{-1} M^{-1}$ | $\lambda_A$(max), nm | $\epsilon$, $10^4 cm^{-1} M^{-1}$ | $\lambda_f$(max), nm | $\Phi_f$ | $\lambda_f$(max), nm | $\Phi_f$ |
| THF | 37.4 | 358–427 298 | 3.23 4.04 | 381–419 298 | 3.97 4.13 | 610 478 | 0.000 068 0.000 094 | 602 482 | 0.000 073 0.000 097 |
| CHCl₃ | 39.1 | 428 314 | 3.41 3.54 | | | 519 | 0.000 088 | | |
| CH₂Cl₂ | 41.4 | 419 | 3.52 | | | | | | |
| acetone | 42.2 | 359–431 | 4.85 | 375–421 | 4.89 | 531 | 0.000 082 | 488 | 0.000 061 |
| DMF | 43.8 | 402 301 | 3.41 3.23 | 406 302 | 3.32 3.23 | 492 495 | 0.000 071 0.000 075 | 480 434 | 0.000 073 0.000 082 |
| DMSO | 45.0 | 406 304 | 4.52 3.54 | 410 306 | 4.64 3.97 | 472 | 0.000 11 | 476 | 0.000 094 |
| acetonitrile | 46.0 | 366–421 299 | 4.52 4.06 | 401 300 | 4.63 4.07 | 499 | 0.000 063 | 495 | 0.000 039 |
| isobutanol | 49.0 | 397 301 | 4.02 4.21 | 405 300 | 4.13 4.25 | 551 | 0.000 099 | 548 | 0.000 096 |
| l-butanol | 51.9 | 361–452 282 | 3.89 4.21 | 376–425 297 | 4.05 4.32 | 556 | 0.0001 | 542 | 0.000 11 |
| ethanol | 55.5 | 356–419 298 | 3.01 2.82 | 401 299 | 3.12 2.96 | 550 | 0.000 053 | 537 | 0.000 055 |
| methanol | | 367–422 296 | 3.07 3.75 | 398 | 3.31 3.76 | 541 | 0.000 027 | 499 | 0.000 027 |

FIG. 6

| solvent | $E_t^2$ | $\lambda_A$ max[3] nm | $\varepsilon$ $10^4 cm^{-1}M^{-1}$ | $\lambda_A$ range[4] nm | $\lambda_F$ max nm | $\Phi_F^5$ | $\lambda_F$ range[4] nm |
|---|---|---|---|---|---|---|---|
| heptane | 30.9 | 425 | 7.25 | 190 - 505 | 595 | 0.082 | 575 - 740 |
| | | 305 | 6.18 | | 579 | 0.079 | |
| toluene | 33.9 | 422 | 7.17 | 190 - 495 | 601 | 0.041 | 510 - 730 |
| | | 314 | 6.28 | | | | |
| benzene | 34.5 | 420 | 11.93 | 190 - 495 | 606 | 0.057 | 520 - 730 |
| | | 318 | 9.37 | | | | |
| THF | 37.4 | 412 | 6.52 | 190 - 510 | 596 | 0.0067 | 450 - 760 |
| | | 306 | 4.75 | | | | |
| ethyl acetate | 38.1 | 410 | 8.51 | 190 - 495 | 624 | 0.0086 | 440 - 725 |
| | | 310 | 6.05 | | | | |
| $CHCl_3$ | 39.1 | 422 | 5.92 | 190 - 505 | 666 | 0.0061 | 460 - 780 |
| | | 316 | 4.69 | | | | |
| $CH_2Cl_2$ | 41.4 | 422 | 6.94 | 190 - 505 | 657 | 0.0051 | 450 - 670 |
| | | 316 | 4.72 | | | | |
| acetone | 42.2 | 410 | 6.74 | 190 - 495 | 468 | 0.0053 | 430 - 565 |
| DMF | 43.8 | 468 | 3.29 | 190 - 515 | 473 | 0.0039 | 405 - 510 |
| | | 364 | 7.32 | | | | |
| DMSO | 45.0 | 390 | 4.49 | 190 - 510 | 480 | 0.0021 | 425 - 545 |
| | | 310 | 3.47 | | | | |
| acetonitrile | 46.0 | 398 | 4.53 | 190 - 495 | 473 | 0.0014 | 430 - 585 |
| | | 316 | 3.41 | | | | |
| n-butanol | 50.2 | 406 | 4.57 | 190 - 490 | 586 | 0.0019 | 432 - 705 |
| | | 316 | 2.82 | | | | |
| ethanol | 51.9 | 394 | 6.39 | 190 - 490 | 482 | 0.0016 | 425 - 690 |
| | | 318 | 4.08 | | | | |
| methanol | 55.5 | 392 | 4.67 | 190 - 485 | 490 | 0.00068 | 425 - 545 |
| | | 318 | 2.85 | | | | |

FIG. 10

| solvent | Detection limit in nm$^2$ | % decomposition over 5 min |
|---|---|---|
| heptane | 0.015 | 1 |
| THF | 12 | 4 |
| CHCl$_3$ | 0.95 | 3 |
| acetone | 14 | 4 |
| DMF | 17 | 3 |
| acetonitrile | 89 | 2 |
| ethanol | 128 | 2 |
| methanol | 205 | 5 |
| water | 625 | 4 |

FIG. 11

| solvent | detection limit in nM | | | | photostability in % deviation | | | |
| --- | --- | --- | --- | --- | --- | --- | --- | --- |
| | 1 | 2 | 3 | 4 | 1 | 2 | 3 | 4 |
| heptane | | | 0.002 | 0.011 | | | 1 | 1 |
| THF | 70 | 62 | 14 | 12 | 5 | 1 | 1 | 2 |
| CHCl$_3$ | | 79 | 0.28 | 0.85 | | 8 | 13 | 9 |
| acetone | 74 | 58 | 14 | 20 | 5 | 4 | 4 | 3 |
| DMF | 350 | 165 | 49 | 61 | 4 | 1 | 2 | 2 |
| acetonitrile | 240 | 230 | 220 | 240 | 2 | 2 | 3 | 4 |
| ethanol | 170 | 120 | 62 | 93 | 3 | 2 | 2 | 2 |
| methanol | 510 | 290 | 160 | 380 | 7 | 9 | 2 | 2 |

FIG. 13 normal light under UV lamp

FLUORESCENT DYE

This appln is a C-I-P of Ser. No. 09/017,518 filed Feb. 2, 1998.

DESCRIPTION

1. Technical Field

The present invention relates to a new class of solvent matrix sensitive dyes which possess reactive linkers for attachment to nucleic acids, carbohydrates and peptides. These derivatives operate in the visible and UV spectrum. In particular, uses for the dyes include single molecule spectroscopy and fluorescence, the labelling of proteins, DNA, and carbohydrate, and assaying enzymatic activity.

2. Background

What is needed is a new class of intramolecular charge-transfer labels which absorb visible and ultraviolet light, display a dramatic solvent sensitivity and can be detected at the single molecule level for labelling proteins, nucleic acids, and carbohydrates and for assaying enzymatic activities.

SUMMARY OF THE INVENTION

The invention is directed to specific fluorescent dyes which have reactive linkers for conjugating to nucleic acids, carbohydrates and peptides. The conjugates fluoresce in the visible and UV spectrum and have an excellant solvochromatic response as compared to other fluorescence or chromatic labels. The conjugates are stable but also have medium sensitive. The fluorescent dyes have little triplet state formation and are not photoreactive, making them an excellent substance for biological investigations. Uses for the dyes include protein labelling, DNA labelling, single molecule spectroscopy and fluorescence. A synthesis of the dyes and of dye conjugates is disclosed. Methods of use include the detection of carbohydrate-protein interactions.

One aspect of the invention is directed to a fluorescent dye represented by the following structure:

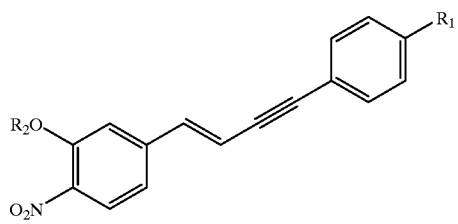

$R_1$ is selected from the group consisting of radicals represented by the following structures:

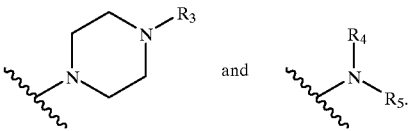

$R_2$ and $R_3$ are independently selected from a group consisting of hydrogen and radicals represented by the following structures:

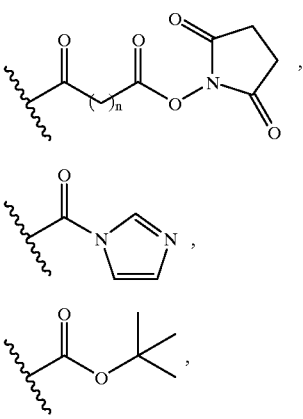

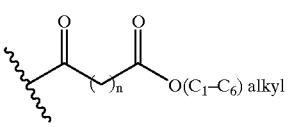

wherein $1 \leq n \leq 4$. $R_4$ and $R_5$ are independently selected from the group consisting of C1–C6 alkyls. Preferred embodiments of this aspect of the invention are fluorescent dyes represented by the following structures:

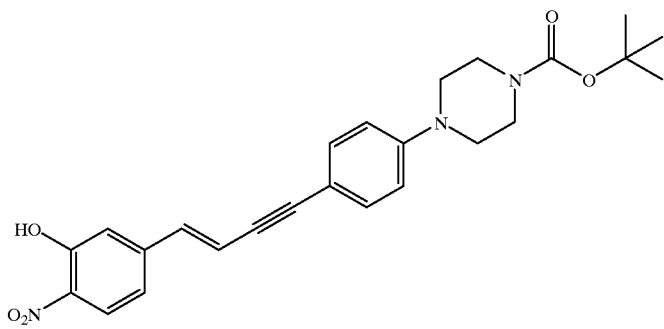

-continued

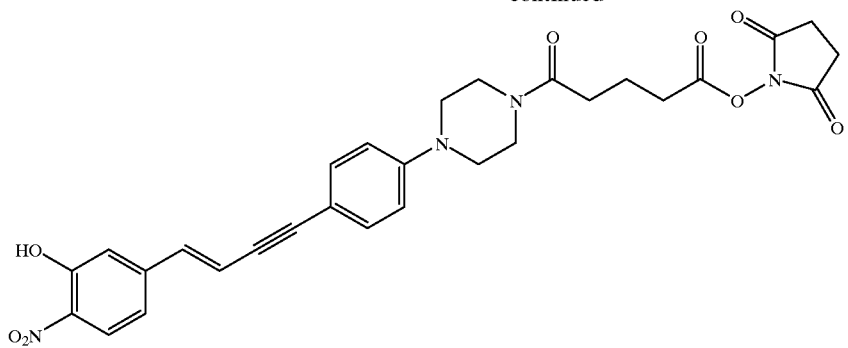

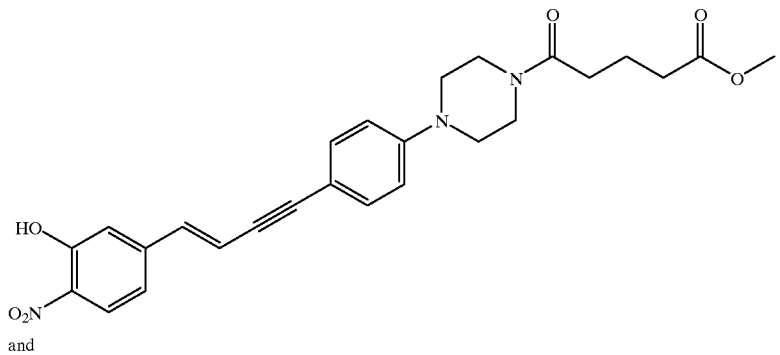

and

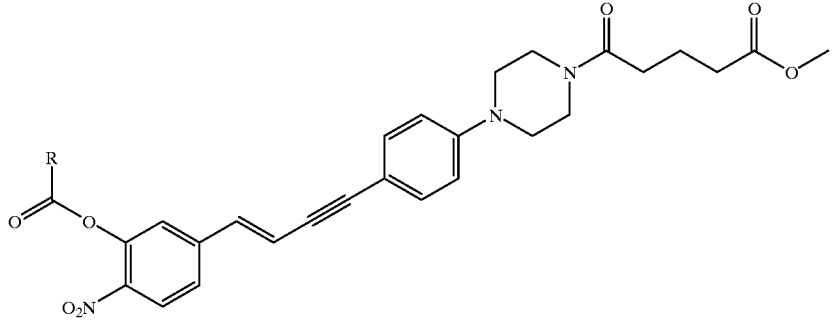

wherein R is selected from a group consisting of

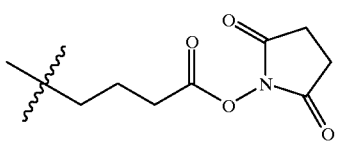

and

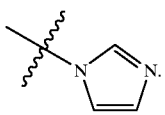

Another aspect of the invention is directed to a fluorescent conjugate represented by D-L-B. D- is a fluorescent dye having a radical portion and is represented by the following structure:

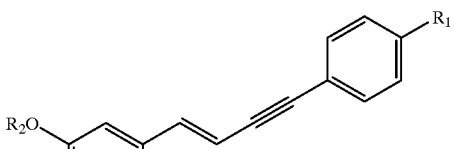

$R_1$ is selected from the group consisting of radicals represented by the following structures:

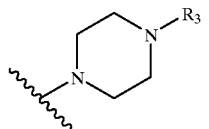 and 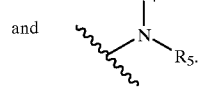

$R_4$ and $R_5$ are independently selected from the group consisting of C1–C6 alkyls and $R_2$ and $R_3$ are independently either hydrogen or absent so as to form a radical, with a proviso that one of $R_2$ and $R_3$ is absent so as to form the radical of the fluorescent dye. -L- is a diradical linker selected from a group represented by the following structures:

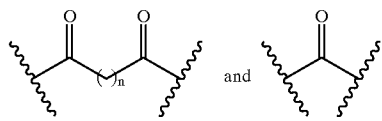

wherein 1≦n≦4. -B is a biomolecule having a radical portion, wherein the radical portion is selected from a group consisting of hydroxyl radical and amino radical. The diradical linker -L- links the radical of the fluorescent dye D- to the radical of the biomolecule -B to form the fluorescent conjugate. In preferred embodiments, the biomolecule is selected from a group consisting of carbohydrate, nucleic acid, and peptide. Examples of preferred embodiment are represented by the following structures:

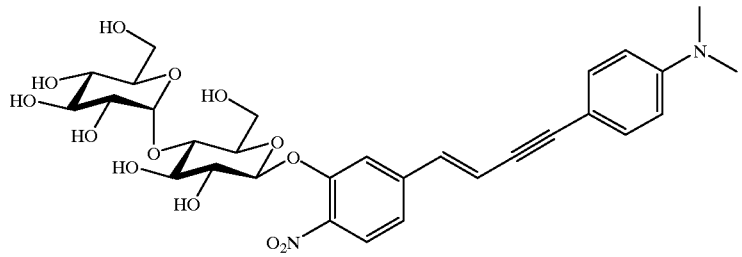

and

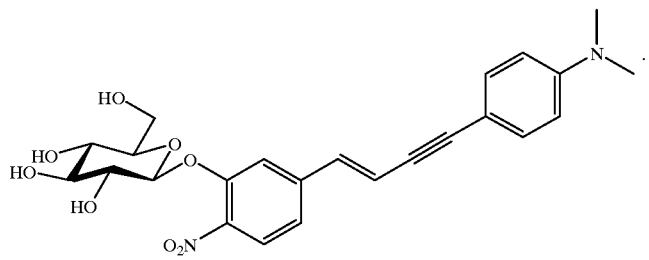

Another aspect of the invention is directed to a fluorescent conjugate represented by D-B. D- is a radical of a fluorescent dye represented by the following structure:

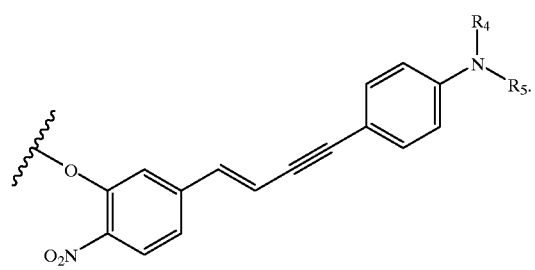

$R_4$ and $R_5$ are independently selected from the group consisting of C1–C6 alkyls. -B is a biomolecule having a radical portion, wherein the radical portion is selected from a group consisting of hydroxyl radical and amino radical. The radical of the fluorescent dye D- is linked to the radical portion of the biomolecule -B to form the fluorescent conjugate. In preferred embodiments, fluorescent conjugate the biomolecule is selected from a group consisting of carbohydrate, nucleic acid, and peptide.

Another aspect of the invention is directed to a fluorescent conjugate represented by $B_1$-L-D-L-$B_2$. D- is a fluorescent dye having two radicals portions and is represented by the following structure:

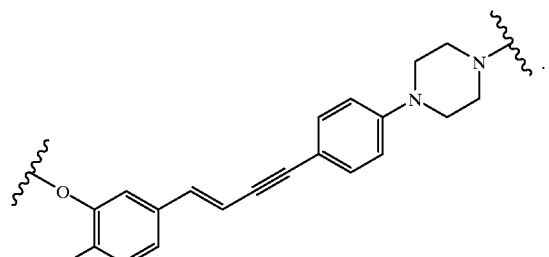

-L- is a diradical linker selected from a group represented by the following structures:

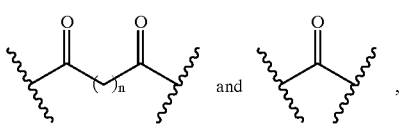

wherein $1 \leq n \leq 4$. $B_1$- and $-B_2$ are independently selected from a group of biomolecules, each biomolecule having a radical portion, wherein the radical portion is selected from a group consisting of hydroxyl radical and amino radical. The diradical linker -L- links each of the radicals of the fluorescent dye D- to the radical of each of the biomolecules $B_1$- and $-B_2$ to form the fluorescent conjugate. In preferred embodiments, each of the biomolecules $B_1$- and $-B_2$ are independently selected from a group consisting of carbohydrate, nucleic acid, and peptide.

Another aspect of the invention is directed to a fluorescent conjugate represented by $B_1$-D-L-$B_2$. D- is a fluorescent dye having a hydroxyl radical and an amino radical and is represented by the following structure:

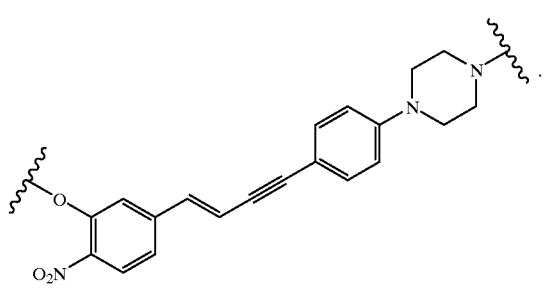

-L- is a diradical linker selected from a group represented by the following structures:

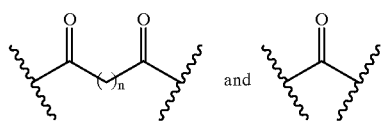

wherein $1 \leq n \leq 4$. $B_1$- and $-B_2$ are independently selected from a group of biomolecules, each biomolecule having a radical portion, wherein the radical portion is selected from a group consisting of hydroxyl radical and amino radical. The diradical linker -L- links the amino radical of the fluorescent dye D- to the radical of the biomolecule $-B_2$ and the hydroxyl radical of the fluorescent dye D- is linked directed to the radical of the biomolecule $-B_1$. In preferred embodiments, the biomolecules $B_1$- and $-B_2$ are independently selected from a group consisting of carbohydrate, nucleic acid, and peptide.

Another aspect of the invention is directed to a fluorescent conjugate represented by $D_1$-B-$L_2$-$D_2$. $D_1$ is a radical of a fluorescent dye represented by the following structure:

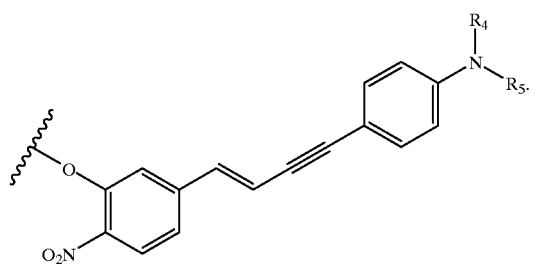

$R_4$ and $R_5$ are independently selected from the group consisting of C1–C6 alkyls. $D_2$ is a fluorescent dye having a radical portion and is represented by the following structure:

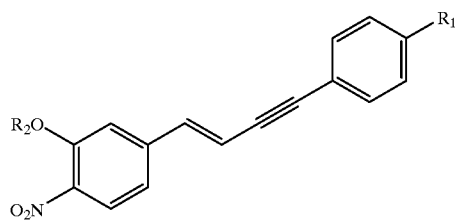

$R_1$ is independently selected from the group consisting of radicals represented by the following structures:

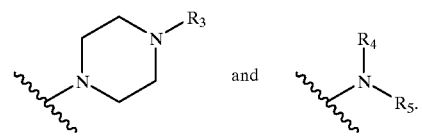

$R_2$ and $R_3$ are independently either hydrogen or absent so as to form a radical. However, there is a proviso that, within each of $D_1$ and $D_2$, one of $R_2$ and $R_3$ is absent so as to form the radical of the fluorescent dye. $L_1$ and $L_2$ are each diradical linkers independently selected from a group represented by the following structures:

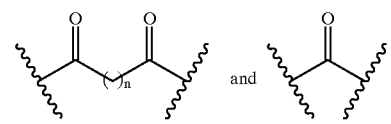

wherein $1 \leq n \leq 4$. -B is selected from a group of biomolecules, each biomolecule having a first and a second radical portion, wherein the first and second radical portions are independently selected from a group consisting of hydroxyl radical and amino radical. The fluorescent dye $D_1$ is linked to the first radical of the biomolecule by the diradical linker -L-. The fluorescent dye $D_2$ is linked to the second radical of the biomolecule by the diradical linker -L- to form the fluorescent conjugate. In preferred embodiments, the biomolecule B- is selected from a group consisting of carbohydrate, nucleic acid, and peptide.

Another aspect of the invention is directed to a method for identifying an interaction between a dye labeled biomolecule and a binding molecule. In the first step of the method, a dye labeled biomolecule is provided wherein the dye labeled biomolecule is selected from a group consisting of one of the following structures:

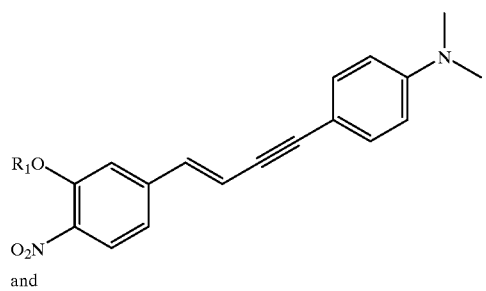

and

-continued

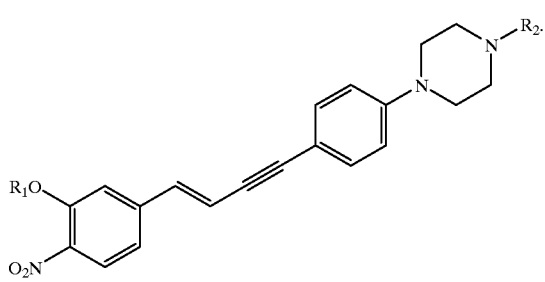

$R_1$ and $R_2$ are each independently selected from a group consisting of hydrogen, a carbohydrate, a nucleic acid, a peptide and a radical represented by one of the following structures:

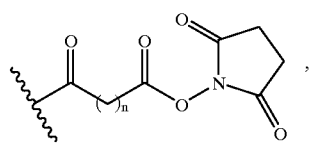

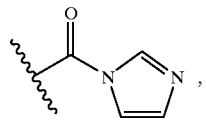

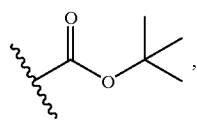

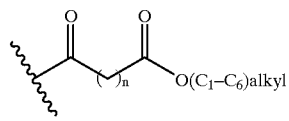

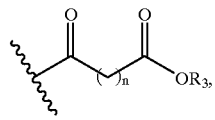

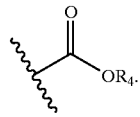

$R_3$ and $R_4$ are each independently selected from a group consisting of hydrogen, a carbohydrate, a nucleic acid and a peptide; $1 \leq n \leq 4$. Then, the dye labeled biomolecule is admixed with a binding molecule. And then, a binding event is selectively detected between the dye labeled biomolecule described above and the binding molecule.

Another aspect of the invention is directed to a method for synthesizing a dye molecule represented by the following structure:

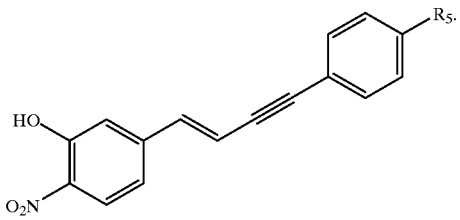

$R_5$ is selected from a group consisting of one of the following structures:

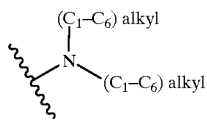

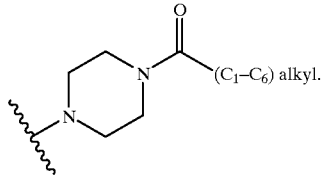

In the first step of the method, an aldehyde molecule is provided wherein the aldehyde molecule is represented by the following structure:

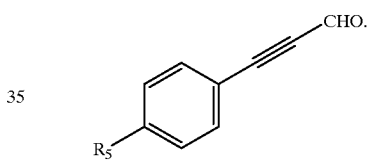

Then, the above aldehyde molecule is condensed with a phosphodiester represented by the following structure:

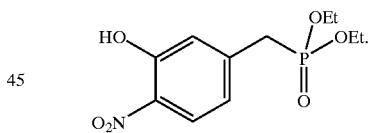

The product is the desired dye molecule.

Another aspect of the invention is directed to a method for detecting an enzyme having a hydrolytic activity with respect to a biomolecule. A sample which potentially includes the enzyme is admixed with a fluorescent conjugate under reaction conditions within an aqueous phase. The fluorescent conjugate is of a type described described above wherein the biomolecule is conjugated to a fluorescent dye. However, in this instance, the biomolecule is hydrolyzable by the enzyme so as to form a fluorescent fragment which includes the fluorescent dye and which is solvatochromic and separable from the fluorescent conjugate by transfer from the aqueous phase into an organic phase of a biphasic mixture. The fluorescent conjugate is then enzymatically hydrolyzed within the above admixture for forming the fluorescent fragment. The newly formed fluorescent fragment is then transferred from the aqueous phase into the organic phase of the biphasic mixture. Finally, the fluorescent fragment transferred into the organic phase is detected for indicating the presence of the enzyme within the sample. In a preferred mode, the organic phase is an oil and a fluorescence enhancement is achieved by use of a volumetric ratio of the organic phase to the aqueous phase of the biphasic mixture of 1/100 or less. The preferred volumetric ratio is 1/200. Preferred biomolecules include carbohydrates, nucleic acids, peptides, and phosphoric biomolecules, and are employed for detecting glycosidase, alkaline phosphatase, and protease.

BRIEF DESCRIPTION OF FIGURES

FIG. 6 shows a table of absorbtion maxima, extinction coefficient, fluorescence maximum and quantum yield of glycodyes 1 and 2.

FIG. 10 illustrates a table which shows UV/Visible Absorption Maxima, Range, Extinction Coefficients (ε), Fluorescence Maxima, Range and Quantum Yields (($\Phi_f$) for Compound 1000 in Various Anhydrous Solvents with the following footnotes:[a] Data provided is average over several iterations with a deviation within 5%. Although unavoidable, traces of moisture undoubtedly decreased the intensity of these values. Caution was taken to minimize contact with moisture and all solvents were either purchased dry and or distilled. [b] See Reichardt, Chem. Rev. 1994, 94, 2319; [c] The K-band is defined as the lower and the B-band as the higher wavelength band; [d] Range is defined as the region in which 5% of the maximum absorption was apparent; [e] The quantum yields were standardized against 0.70 for rhodamine B in ethanol.

FIG. 11 illustrates single Molecule Detection of Compound 1000 with the following footnotes: [a] Excitiation was provided with an argon ion laser at 455 nm (0.5 mW) and the fluorescence was filtered with a 545 nm cutoff filter; [b] Detection limit is given as the concentration at which transients from single molecules were no longer resolved from the baseline.

FIG. 13 illustrates the behavior of compounds 1–4 in the Eigen-Rigler confocoal fluorescence correlation spectrometer wherein excitiation was provided with at 455 nm (0.5 mW) and the fluorescence was collected through a 545 nm cutoff filter.

DETAILED DESCRIPTION OF THE INVENTION

The invention is directed to the construction of a family of DHNB (1-[4-(N,N-dimethylamino)-phenyl]-4-(3- hydroxy-4-nitrophenyl)-3-(E)-buten-1-yne (compound 4)) derivatives which can be used to label a wide variety of biologically-significant molecules.

The labeling of molecules with charge-transfer dyes, such as 5-(dimethylamino)-1-napthalenesulfonyl (dansyl) chloride, is a powerful tool for examining the solvent shell of attached substances. The present invention involves the synthesis and application of a new charge transfer label, based on p-(N,N-dimethylamino)-p'-nitro-trans-trans-1,4-diphenyl-1,3-butadiene (NND) (Shin et al. J. Phys. Chem. 1988, 92, 2945). Unlike many commonly used fluorophores, the quantum yield of NND decreases over four orders of magnitude upon changing from non-polar to polar environments. In addition, several derivatives of NND undergo little photodecomposition and can be detected at the picomolar level in a confocal fluorescence correlation spectrometer.

Figure 1:
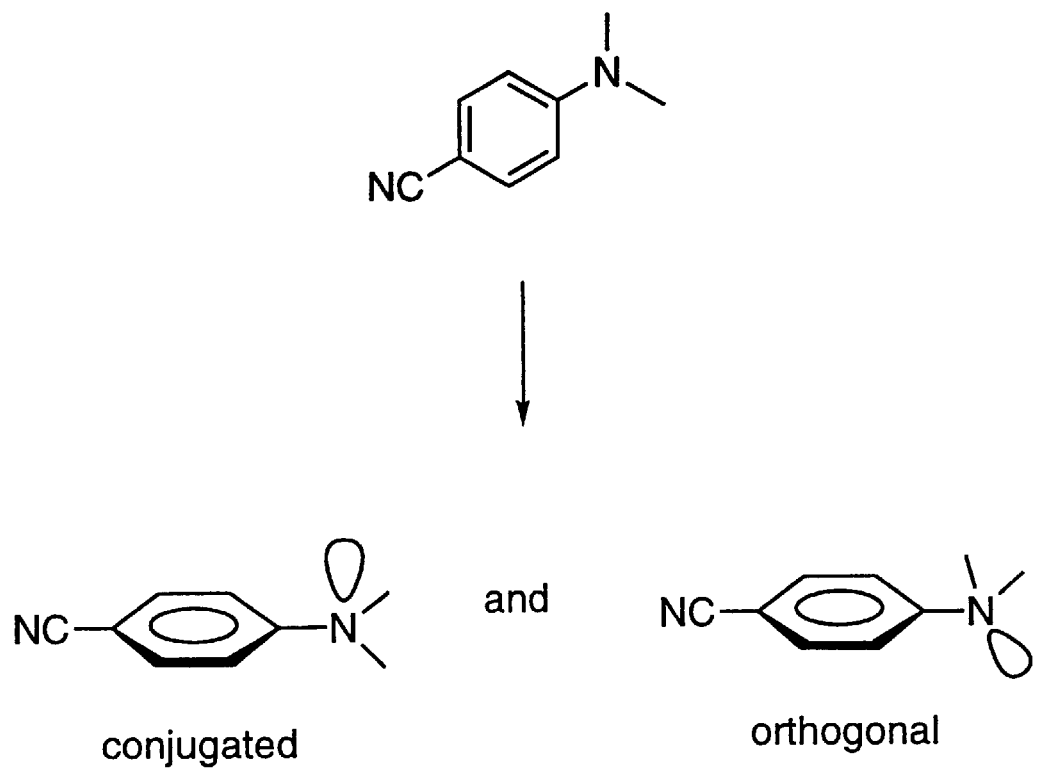
FIG. 1 illustrates observation of states seen in the fluorescence spectrum of p-N,N-dimethylaminobenzonitrile and attributed internal twisting about the dimethylamino group through analogy to several locked and rotationally restricted derivatives.
Figure 1:
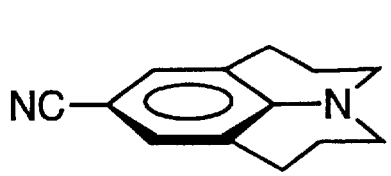
Figure 1:
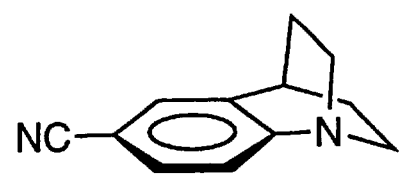
Figure 2:
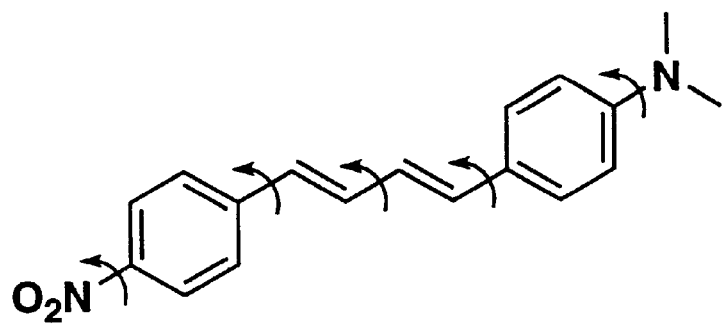
FIG. 2 illustrates the synthesis of two analogs of NND, compound 3 and compounds 4. Compound 4 is the title compound: 1-[4-(N,N-dimethylamino)-phenyl]-4-(3-hydroxy-4-nitrophenyl)-3-(E)-buten-1-yne (DHNB).
Figure 2:
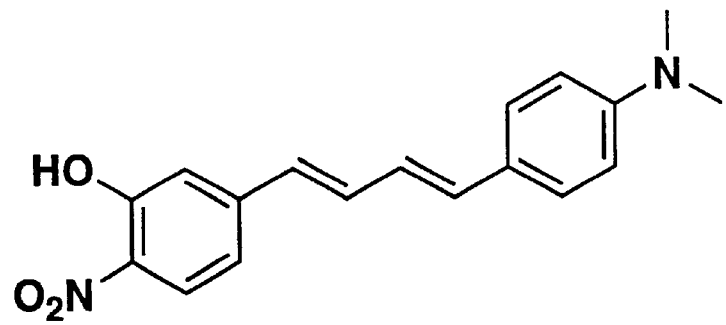
Figure 2:
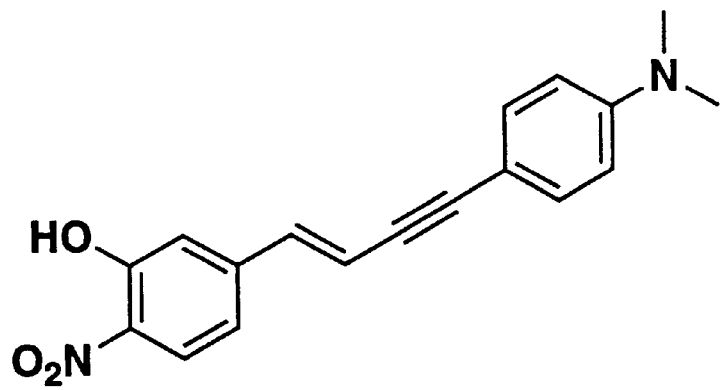

In conjunction with recent detection of single molecules in solution, one aspect of the invention, as described in example 1, below, describes a method to discriminate between single free and carbohydrate-bound aggregates of the Jack Bean lectin, Concanavalin A (Con A) using a derivatized NND label. To this end, derivatives of NND were constructed possessing an additional functional handle. One derivative, alkenyne 4 (example 1; FIG. 2), was efficiently attached to the β-anomeric position of glucopyranosides. Transients from single aggregates of this fluorophore were detected in solutions which contained both Con A and maltosid 1, and not the corresponding glucoside 2. This result is in agreement with the known affinity of Con A for α-glucopyranosides and not β-glucopyranosides. A full description of the synthesis of these dyes including modifications which enhance solubility and linkage to form the title DHNB derivatives, their solvochromatic properties and the method used for single aggregate detection is provided in examples 1 and 2 below.

EXAMPLE 1

Detection of Carbohydrate-Protein Interactions at the Molecular Level

We have applied fluorescence response to distinguish between the environment surrounding a carbohydrate as it passes from saline solution to the surface of a protein. Since many carbohydrate-protein complexes exist in aggregated forms, the appended fluorophore will respond not only to the surface interaction with the protein but also the spatial considerations imparted by inclusion in an aggregate. In addition, this aggregation increases the number of fluorescent units per molecular entity, as each aggregate can contain up to one ligand per protein. This example examines the lectin Concanavalin A (Con A) since its carbohydrate affinity has been determined, it is known to exist as a tetramer at pH 7.2 and its binding pocket has been reported to be more hydrophobic than predicted.

The first steps towards this method required derivatization of NND (p-(N,N-dimethylamino)-p'-nitro-trans-trans-1,4-diphenyl-1,3-butadiene) so that it could be attached to carbohydrates.
Results:

We begin with the synthesis of two analogs of NND, compounds 3 and 4 (FIGS. 2–5), which contain a phenolic handle for linkage to the anomeric center of a carbohydrate. Prior to this work, Aykiyama reported that NND can be converted to 3 by exposing its DME solution to potassium tert-butoxide in air (Akiyama et al. M. Bull. Chem. Soc. Japan 1995, 68, 2043). This procedure provided a 13% yield of 3 along with several alkynic products from oxidation of the internal alkenes. The synthetic approach employed herein uses a direct construction providing 3 and 4 in significantly higher overall yield and without the need for tedious chromatographic separation. This was accomplished through coupling of phosponate 8 with the corresponding aldehydes 9 and 13 by means of a Wadsworth-Horner-Emmons modified Wittig reaction. This disconnection was chosen based on the high trans-stereoselectivity of this method and the fact that aldehyde 9 is commercially-available and the other materials were obtained in three steps. Phosphonate 8 was prepared through functional manipulation of aldehyde 5. This sequence began by reducing carbonyl group in 5 with NaBH4 as described in FIG. 3. The resulting alcohol 6 was then converted to bromide 7 using the phosphonium salt method of Appel (Appel et al. Angew. Chem. Int. Ed. Engl. 1975, 14, 801). In turn, this bromide was displaced with triethylphosphite at 150° C. in DMF providing phosphonate 8. This sequence was readily conducted on a 10 g scale with an 83% overall yield. In accordance with Wadsworth-Horner-Emmons modified Wittig procedure, the ylid of 8 was generated by the addition of 2.2 equivalents of NaHMDS in THF to the crude displacement mixture at 0° C. The production of a deep purple color upon surpassing addition of first equivalent of base provided a convenient internal standard. Condensation of this dianion with p-N,N-dimethylaminocinnamaldehyde (9) provided a 54% yield of NND—OH (3).

Numerous methods were examined for attaching 3 to the anomeric center of carbohydrates (Paulsen et al. Chem. Soc. Rev. 1989, 61, 1257; Hale et al. The Chemistry of Natural Products; Thompson, R. H., Ed.; Chapman and Hall, 1985, pp 1–59; Schmidt et al. Comprehensive Organic Synthesis; Trost, B. M., Fleming, I., Eds.; Permagon Press: Oxford, 1991; Vol 6, pp 33–64; Toshima et al. Chem. Rev. 1993, 93, 1503). Unfortunately, NND—OH (3) decomposed under the conditions generated during activation of phenylthio, phenylselenyl, fluoro and pentenyl glycosides. Classical Konigs-Knorr coupling with α-D-glucopyranosylbromide tetraacetate either resulted in recovery or slow decomposition of 3. Recently, Roy developed a phase transfer method which primarily operates through an SN2 displacement of a glycosyl bromide by a phenolate (Roy et al. Synth. Comm. 1990, 20, 2097; Roy et al. Glycoconjugate J. 1991, 8, 75; Roy et al. J. Chem. 1991, 69, 817). This method provided a high degree of stereoinversion and was amenable to several carbohydrate and phenolic units. Application of this method to NND—OH (3) was complicated by the low solubility of 3 in applicable solvents. At saturation in methylene chloride, glycosylation of 3 was only 20% complete after 2 weeks. In addition, purification of this material was complicated by the presence of several unwanted side-products which arose from in situ acetate-hydrolysis and further reaction with a-D-glucopyranosylbromide tetraacetate. In an attempt to improve the efficiency of this process, attention was turned to construction alkyne 4, with the hope that it would be more soluble.

Figure 4:
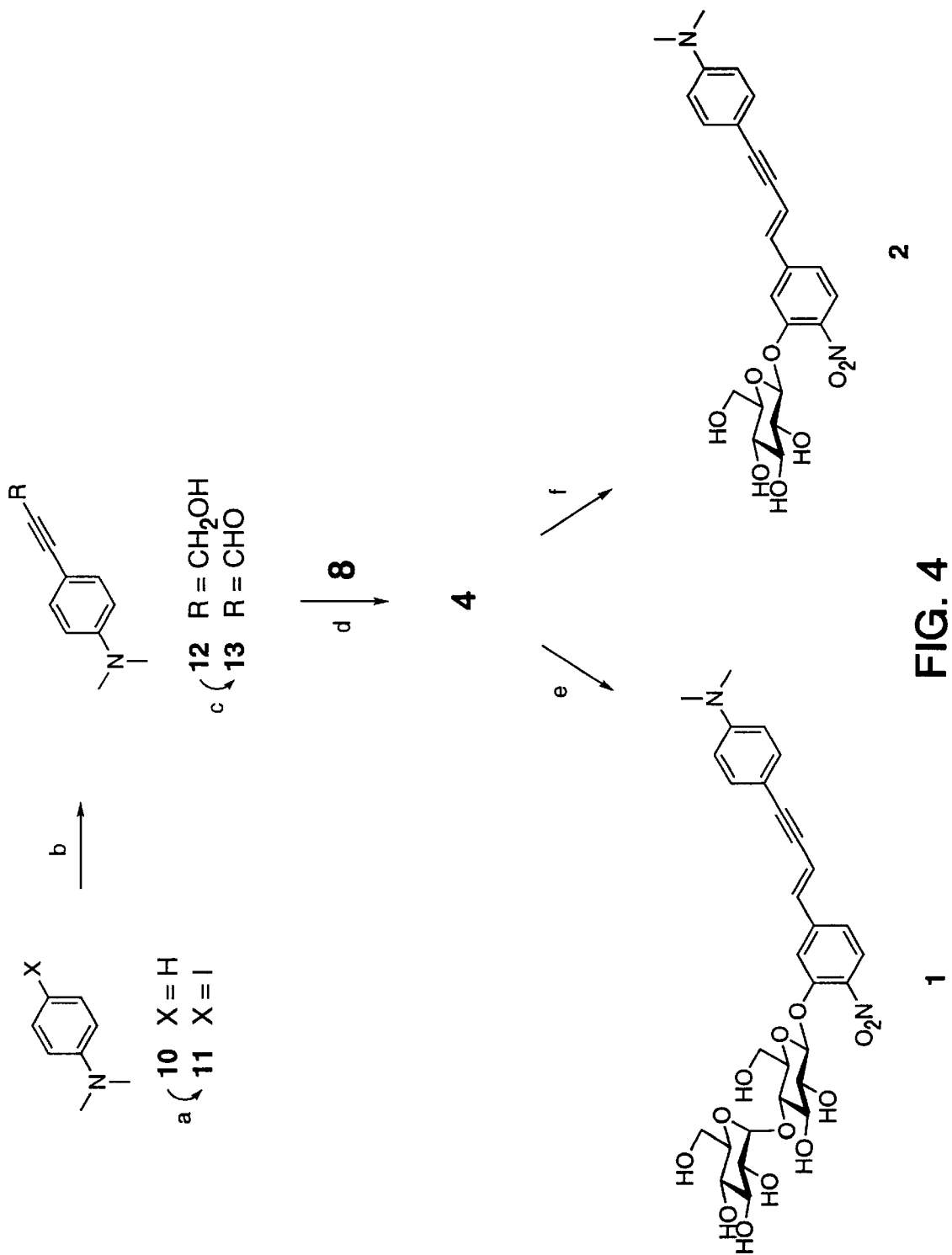
FIG. 4 illustrates the synthesis of 1, 2 and 4 with the following steps:(a) i. iodine, $NaHCO_3, H_2O$, 12–15° C., 10 min; ii. then room temperature, 1 hour, 86%. (b) propargyl alcohol, $Cl_2Pd(PPh_3)_2$ (1.4 mol %), CuI (1.4 mol %), $Et_3N$, room temperature, 18 hours, 89%. (b) $MnO_2$, $CH_2Cl_2$, room temperature, 4 h, 89%. (d) i. add NaHMDS (2.2 equivalents) in THF to crude 8 in DMF, 0° C. to room temperature, 1 hour; ii. add 13 in THF, −20° C. to room temperature, 6 hours, 56%. (e) i. α-D-maltopyranosylbromide heptaacetate, N-benzyltriethylammonium chloride, 1 M NaOH, $CH_2Cl_2$, room temperature, 12 hours; ii. $NaOCH_3$, $CH_3OH$, room temperature, 1 hour; iii. $PhCO_2H$; iv. powdered 4 Å mol. sieves, 1,4-dioxane, 70° C., 2 h; 69%. (f) i. α-D-glucopyranosylbromide tetraacetate, N-benzyltriethylammonium chloride, 1 M NaOH, $CH_2Cl_2$, room temperature, 12 hours; ii. $NaOCH_3$, $CH_3OH$, $Ph$, room temperature, 1 hour; iii. $PhCO_2H$; iv. powdered 4 Å mol sieves, 1,4-dioxane, 70° C., 2.5 hours; 71%.
Figure 5:
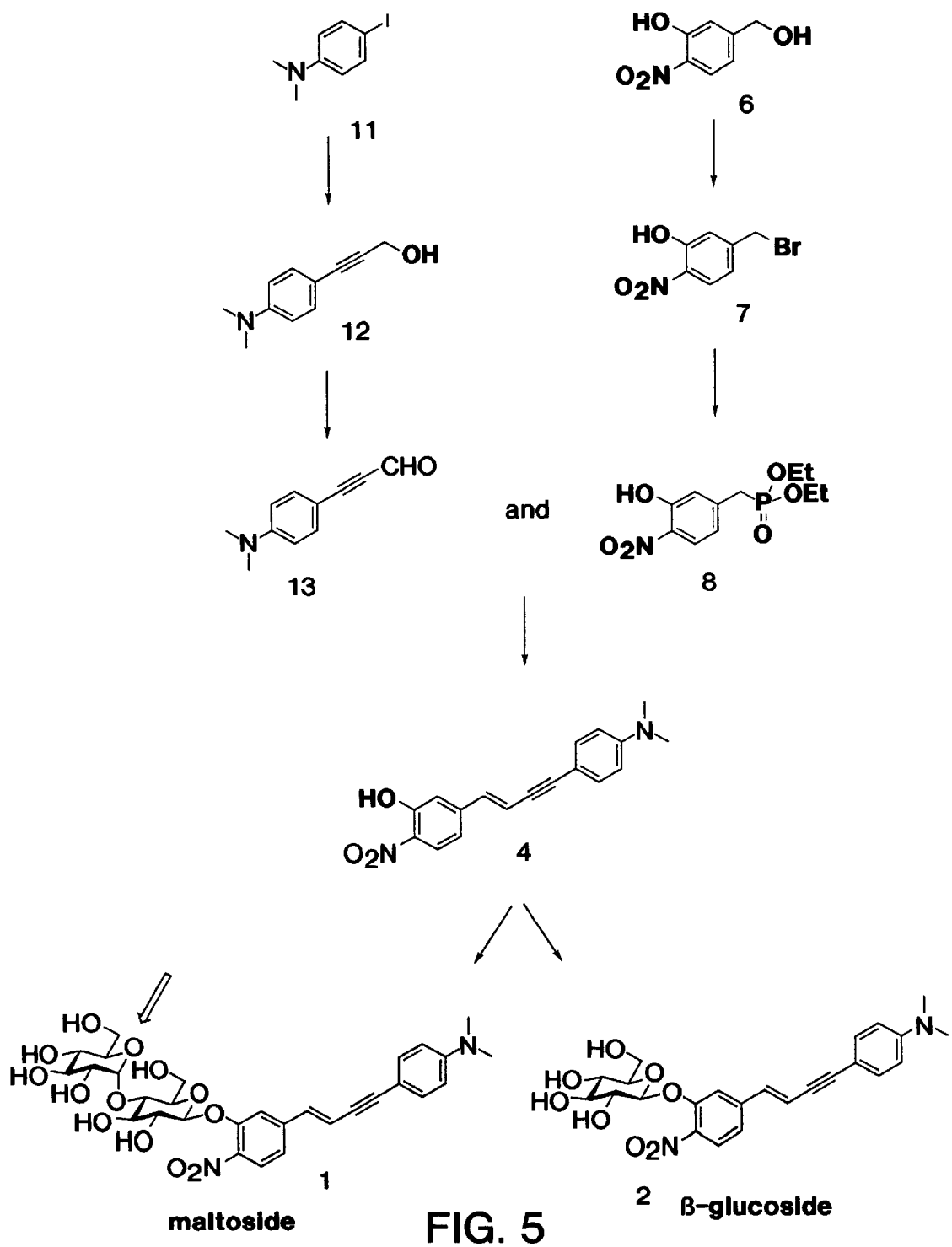
FIG. 5 shows the complete scheme for the synthesis of 1, 2 and 4 wherein the reaction steps, depicted as arrows for each transition, are exactly as described in FIGS. 3 and 4.

Application of the previously described Wittig protocol for 4 required construction of aldehyde 13 (FIG. 4). This material was prepared in three steps from N,N-dimethylaniline (10). The sequence began by regioselectively introducing an iodine atom onto the para-position of 10, through reaction with iodine in an aqueous sodium bicarbonate buffer. Upon one recrystallization from an ether-hexane mix, iodide 11 could be coupled to propargyl alcohol using a procedure described by Takalo and Haenninen (Takalo et al. Acta. Chim. Scand. 1988, B42, 448). The resulting alkynol 12 was then oxidized with a slurry of MnO$_2$ to the desired aldehyde 13. Condensation of this aldehyde with the previously described ylid of 8 provided alkenyne 4, as evidenced by presence of a single 16 Hz vinylic-coupling constant in its $^1$H-NMR spectrum. Unlike NND—OH (3), alkenyne 4 was soluble in methylene chloride up to 0.2 M and readily reacted with 2,3,4,6-tetraacetoxy-α-D-glucopyranosylbromide under the conditions of Roy vida supra. Since partial hydrolysis of the C(6)-acetate often occurred under these conditions, the crude material was directly subjected to methanolysis, providing a single compound, 2 (FIG. 4). Alternatively, buffering of the methanolysis reaction with benzoic acid provided the readily recrystallized benzoate salt of 2. Encouraged by this success, efforts were directed at preparing a derivative which contained an α-glucopyranosidic linkage for binding to Con A (FIG. 4; step e). This was accomplished by appending maltose, as it already contained an a-glucopyranoside and the association constant for the binding of maltose to Con A was determined to microcalorimetrically to be 1.6×103 M-1. 14 g Under conditions previously described for construction of 2, the benzoate of β-maltoside 1 was obtained in 73% from 4 and the corresponding peracetylated α-pyranosylbromide of maltose. The free bases 1 and 2 were obtained by warming solutions of their benzoate salts in 1,4-dioxane containing powdered 4 Å molecular sieves.

The absorption and fluorescence spectra of 1 and 2 were examined in solvents ranging from THF to methanol (FIG. 6). These materials absorbed in two regions, one centered about 390–435 nm and the other between 280–320 nm. The position and intensity of this absorption was nearly identical for both 1 and 2. With the exception of methylene chloride and chloroform, the position of the lower energy band deviated only 3% from ~400 nm and was on average 20–30 nm lower than that of 4. The fluorescence maxima were nearly identical for 1 and 2 and their quantum yields in methanol were 36% and 39% less than that in THF, respectively. In addition, fluorescence from maltoside 1 and glucoside 2 could be detected up to 720 nm in THF, while no fluorescence was detected above 580 nm in methanol. The closest line of an argon laser to the absorption maxima of 1 and 2 was at 457 nm. At this excitation wavelength, the emission from 1 and 2 was ~25% of that at 400 nm in THF. Fluorescence from 1 and 2 in media established for monosaccharide binding to the tetrameric form of Con A (i.e., 0.05 M in PIPES (pH 7.2), 10 mM in MnCl$_2$, 10 mM in CaCl$_2$, and 1 M in NaCl) could not be detected in a SLM-Aminco fluorimeter, even at saturation or at its absorption maximum.

Confocal fluorescence correlation spectrometry was measured using the spectrometer described by Eigen and Rigler (Eigen, M.; Rigler, R. Proc. Natl. Acad. Sci. USA 1994, 91, 5740). Samples of 1–4 were examined in several organic solvents by placing a droplet of the appropriate solution in a ~20 mL conical gold well and bringing the droplet in contact with a thin microscope slide which hung from a water immersible microscope objective by a drop of water. The absorption cross-sectional area for alkenyne 4 at 457 nm is maximally 3×10$^{-16}$ cm$^2$. A laser beam with a single line power of 0.5 mW provides a photon density of 1024 photons/cm$^{2s}$. Within this beam, the singlet excitation rate of this fluorophore would be 3×10$^{-8}$ s$^{-1}$, as given by the product of its cross-sectional area and photon density. Excitation was provided by passing the 457 nm line of an Argon-ion laser through the objective at 0.5 mW. Aqueous solutions were more easily sampled by directly hanging the droplet (approximately 20 mL) from the microscope slide. The resulting fluorescence collected through the same objective by harvesting the emitted photons through a dichroic mirror, followed by filtering with an Omega Optics 545 nm cutoff filter, and counting with a SPAD detector. Autocorrelation was provided online with an ALV-card attached to PC. The fluorescence fluctuation from compounds 1–4 deviated within 5% in most solvents, with the exception of chloroform and methanol. The enhanced decomposition in these solvents can be attributed to slow cleavage of anomeric center by methanolysis or trace acidity often found in chloroform. In the confocal FCS spectrometer, autocorrelation from samples of 3 and 4 was readily detected at the picomolar level in heptane and decreased to nearly the mM level with increased polarity, as reflected by the loss of quantum efficiency. Autocorrelation from 1 and 2 could be detected at a ten-fold lower concentration in THF than in methanol. Samples of 1 and 2 in the buffer commonly used for binding of carbohydrates to Con A did not autocorrelate at any concentration, nor were transients detected as shown in FIG. 12 (Traces A and B). Samples of 51 mM 1, 12 mM 2 and blank fluoresced with a fluctuation of about 5.0, 6.8, and 4.3 kHz respectively. As shown in the upper portion of the trace C (FIG. 12), transients from the diffusion of single molecules containing the fluorophore into the volume element were observed in a solution which contained 170 mM Con A and 51 mM 1 at pH 7.2. The number of molecules in the cavity is N=0.83, as given by N=1/g2, and therefore the concentration of the bound material in this cavity (volume= 2×10$^{-15}$ L) is 0.69 nM. The concentration provided is a description of the Con A-maltoside 1 complex which undergoes fluorescence. The total concentration of the Con A-maltoside 1 complex is much larger and requires knowledge of its quantum yield for determination. Since there is no direct means to determine this yield, the affinity of this interaction cannot be calculated with this method.

Based on the reported affinity of Con A for α-glucopyranosides and lack there of β-glucopyranosides,-the transients seen originate from the complex of 1 with Con A. This was verified by the fact that transients due to aggregates were not detected in samples of 1 without Con A (trace A; FIG. 12) or 2 with and without the addition of Con A (traces B; FIG. 12 and D; FIG. 12, respectively). Transients were also not detected in samples with concentrations of 2 ranging from 0.012 mM upto the point where the background was to large for the detector (~200 mM) with and without Con A. Upon complexation, the weight about the fluorescent label dramatically increases from a formula weight of 632 to approximately 100,000 g/mol. This increase would therefore be translated into a slower diffusion time upon binding, as the diffusion dependent on the size of a material. As given by autocorrelation, the midpoint of descent in the autocorrelated curve is an approximation of the size about the fluorescent moiety. The diffusion times of 1 and 2 ranged between 0.04 and 0.06 ms in various solvents, while that attributed to complexes of 2 with Con A was approximately 19 ms, as seen in FIG. 12. Similar increases in diffusion time have been seen in the complexation of a BODIPY-labeled DNA primer to M13-DNA. 7

Conclusion:

This example describes a new scheme for monitoring interactions between carbohydrates and proteins using 1-[4-(N,N-dimethylamino)-phenyl]-4-(3-hydroxy-4-nitrophenyl)-3-(E)-buten-1-yne (DHNB; compound 4) derivatives. The method provides selective detection of a carbohydrate-bound lectin. Combined with the fact that this fluorescent tag responds not only to solvent polarity but also to confinement, the method should be applicable to a wide variety of events where the label encounters restriction upon binding. Investigations into the reason for this fluorescence enhancement and application this method to study aggregation of these complexes is currently underway.

EXAMPLE 2

Synthesis of a New Class of Solvent Sensitive Fluorescent Labels: SENSI

In example 1 above, we show that the fluorescence from 1-[4-(N,N-dimethylamino)-phenyl)-4-(3-hydroxy-4-nitrophenyl)-3-(E)-buten-1-yne (DHNB; compound 4) is dramatically affected by the nature of its solvent shell, while its UV/visible absorption is minimally altered. For instance, this material absorbs light with a maximum at 421 nm (=50,800 cm-1 M-1) and fluoresces with a quantum efficiency of 0.000017 at 528 nm when dissolved in methanol. However, when placed in a non-polar aprotic solvent such as n-hepane, its absorption maximum is bathochromatically shifted by approximately 15 nm to 435 nm (=47,400 cm-1 M-1) and the quantum yield of its fluorescence is enhanced by approximately 1000 fold to 0.0188 and 0.0205 at 593 and 570 nm, respectively. In an effort to devise new systems for monitoring the interactions of single molecules, this laboratory employed DHNB (compound 4) to selectively detect single bound aggregates of a carbohydrate and protein complex.

This example describes the construction of a family of DHNB derivatives which can be used to label a wide variety of biologically-significant molecules.

Figure 7:
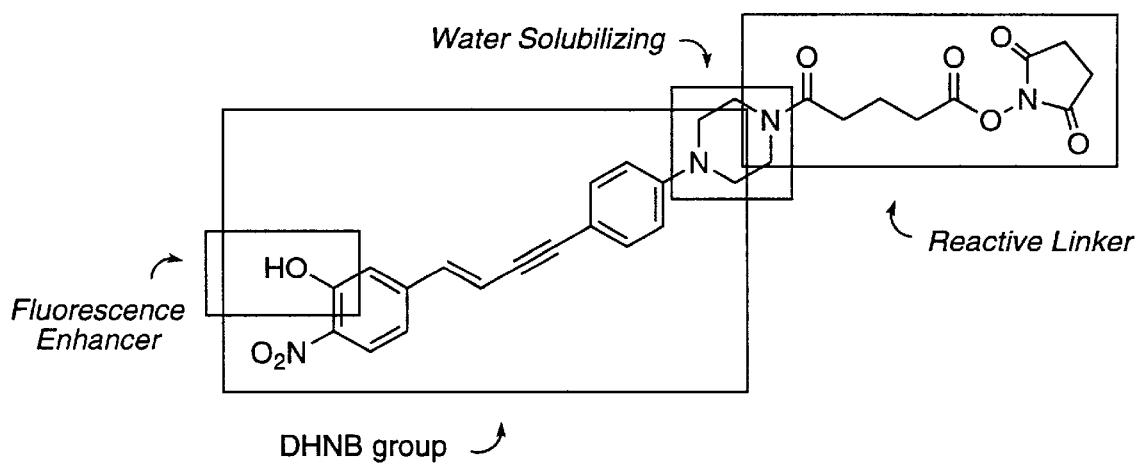
FIG. 7 illustrates the current design mimic strategy which incorporates 1-[4-(N,N-dimethylamino)-phenyl]-4-(3-hydroxy-4-nitrophenyl)-3-(E)-buten-1-yne (DBNB) group, a water solubilizing piperizine linker, a fluorescence enhancer and a reactive linker component.

As displayed in FIG. 7, the current design mimics the functionality contained in the DHNB group (described in example 1). Here, a hydroxyl group was added adjacent to the nitro-group in order to further enhance its fluorescence quantum yield and to serve as a site for attachment of functionality (La Clair, Proc. Natl. Acad. Sci. USA. 1997, 94, 1623–1628; for studies on similar materials see Shin et al. J. Phys. Chem. 1988, 92, 2945; Akiyama et al. Bull. Chem. Soc. Jpn. 1995, 68, 2043).

Figure 8:
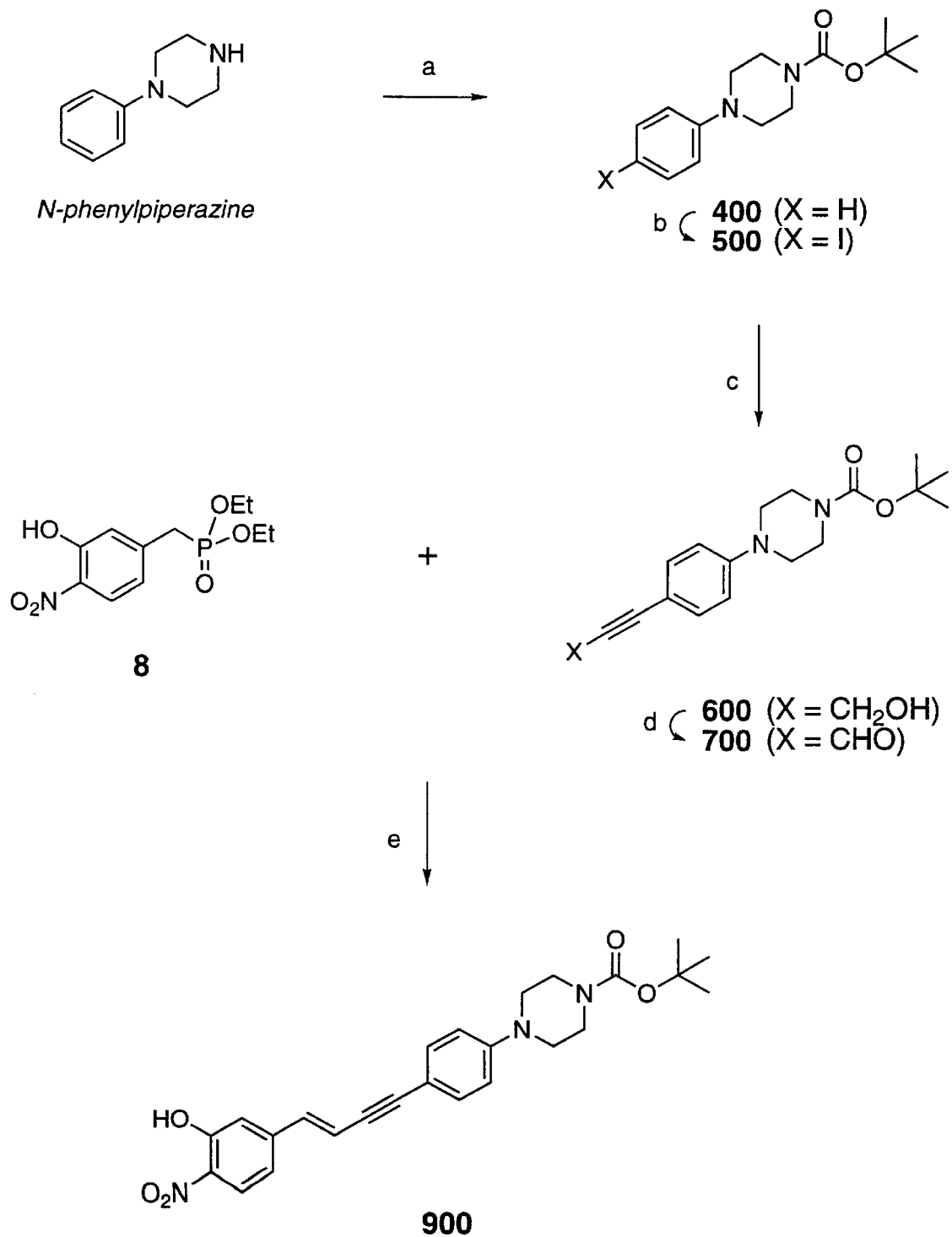
FIG. 8 illustrates the synthesis of compound 900 with the following steps: (a) di-tert-butyl dicarbonate, $Et_3N$, DMAP, $CH_2Cl_2$, 0° C. to room temperature, 94%. (b) 1) iodine, $NaHCO_3$, $CH_2Cl_2$, $H_2O$, 12–15° C., 10 min; 2) then room temperature, 30 min, 90%. (c) propargyl alcohol, $Cl_2Pd$ $(PPh_3)_2$, CuI, $Et_3N$, TBF, room temperature, 18 hours, 85%. (d) $MnO_2$, $CH_2Cl_2$, room temperature, 6 h, 98%. (e) 1) add NaHMDS in THF to 800 in DMF, 0° C. to room temperature, 1 hour; 2) add 700 in THF, −20° C. to room temperature, 8 hours, 62%.

The dimethylamino group of DHNB was now replaced with a piperazine which not only enhances the water solubility of this dye but also provides a handle for linkage. N-Phenylpiperazine was chosen as the starting material for this synthesis, as it is commercially available and inexpensive (~1 DM/g). The synthesis of this model began by halogenating the protected piperazine 400 (The t-boc protected piperazine 400 was prepared by reacting of N-phenylpiperazine with di-t-butyl dicarbonate, triethylamine and DMAP in dichloromethane; for an alternative route see Perez et al. Tetrahedon Lett. 1996, 37, 8487) with iodine in a biphasic mixture of aqueous sodium bicarbonate and dichloromethane, as shown in FIG. 8. Upon one recrystallization, this iodide 500 was coupled using transition metal catalysis to the C-terminus of propargyl alcohol. The resulting alcohol 600 was then oxidized to aldehyde 700 with manganese dioxide, and subsequently condensed with the dianion of phosphate 8, providing 900. The overall yield of this process ranged between 41 and 45% at the 1 g scale.

Figure 9:
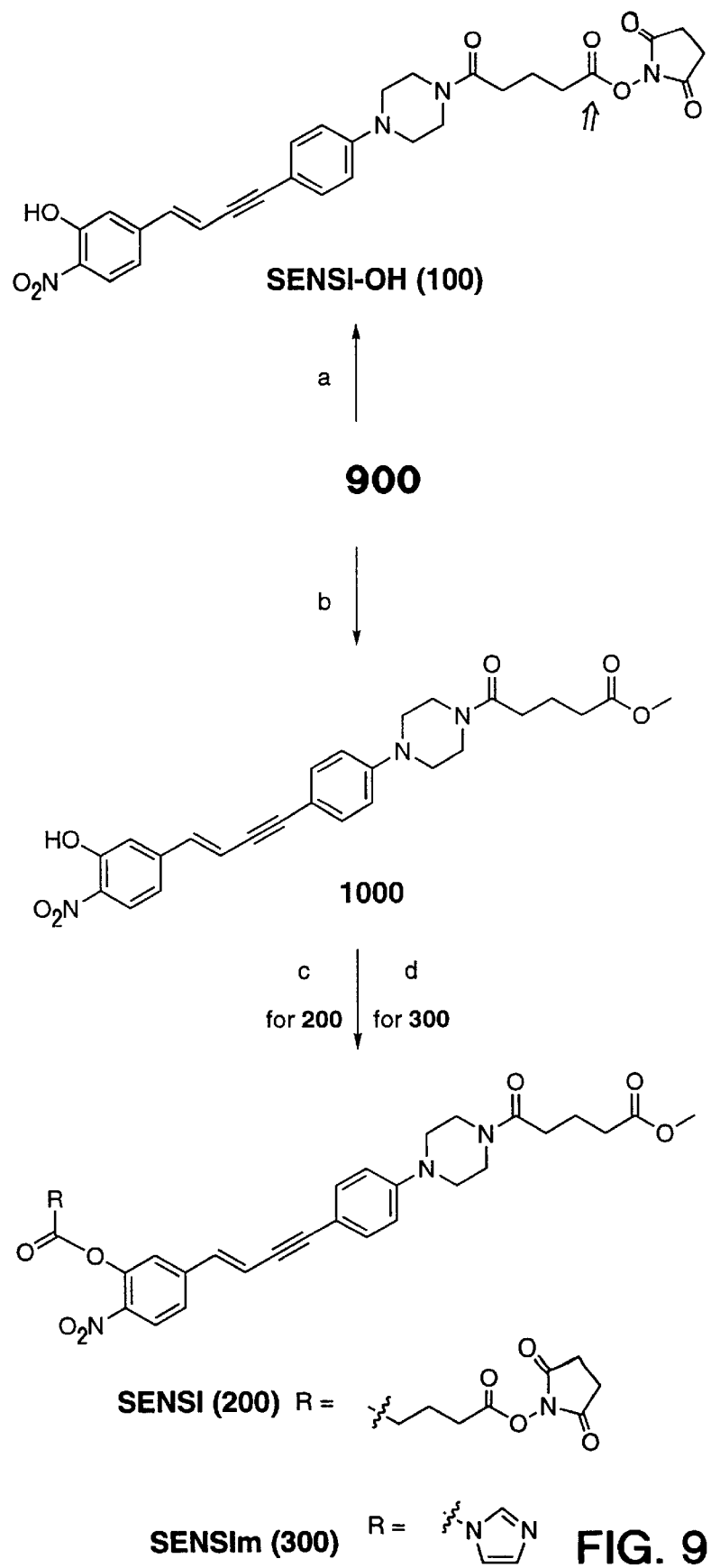
FIG. 9 illustrates the synthesis of compound 100, 200, 300 and 1000 with the following steps: (a) 1) $H_2SO_4$, $H_2O$, THF, room temperature; 2) glutaric anhydride, THF, room temperature, 2 hours; 3) N-hydroxysuccinimide, EDC, THF, room temperature, 12 hours, 81%. (b) 1) $H_2SO_4$, $H_2O$, THF, room temperature; 2) glutaric anhydride, THF, room temperature, 2 hours; iii. EDC, MeOH, TFF, room temperature, 4 hours, 77%. (c) N-hydroxysuccinimidyl glutaryl chloride, DMAP, THF, room temperature, 12 h, 64%. (d) N,N-carbonyldimidazole (2.5 equivalents), DMAP (0.05 equivalents), THF, room temperature, 14 hours, 72%.
Figure 12A:
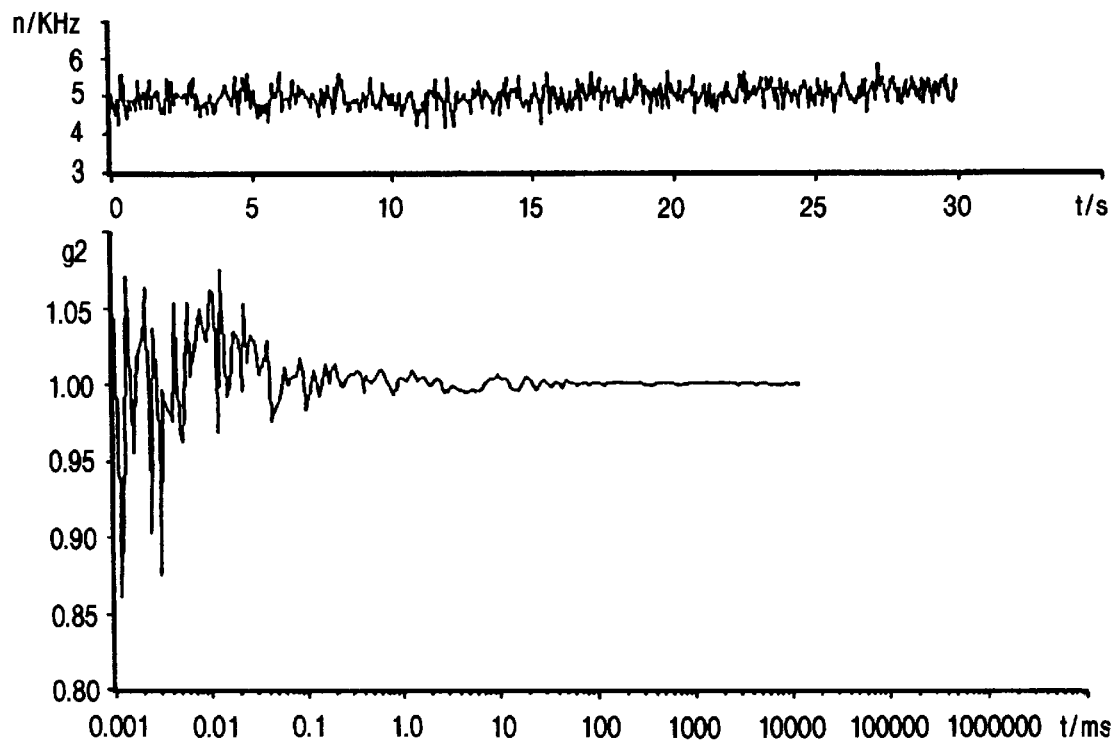
FIG. 12 illustrates real time and autocorrelated traces demonstrating carbohydrate binding to Con A. Samples were in buffer which was 10 mM in $MnCl_2$, 10 mM in $CaCl_2$, 0.05 M in PIPES (pH=7.2) and 1 M in NaCl, irradiated with a laser tuned to 457 nm (0.5 mW) and collected through an Omega Optics 545 cutoff filter. For each sample, the upper trace indicates the frequency of emitted photons (in kHz) and shows transients from aggregates in real time. The lower provides the autocorrelation function, where the number of particles inside the volume element is given by $1/g^2$ as t to 0. The midpoint of the autocorrelated curve provides an approximation of the diffusion time. (A) 51 mM 1, (B) 12 mM2, (C)51 mM 1 with 170 mM Con A and (D) 12 mM 2with 170 mM Con A.
Figure 12B:
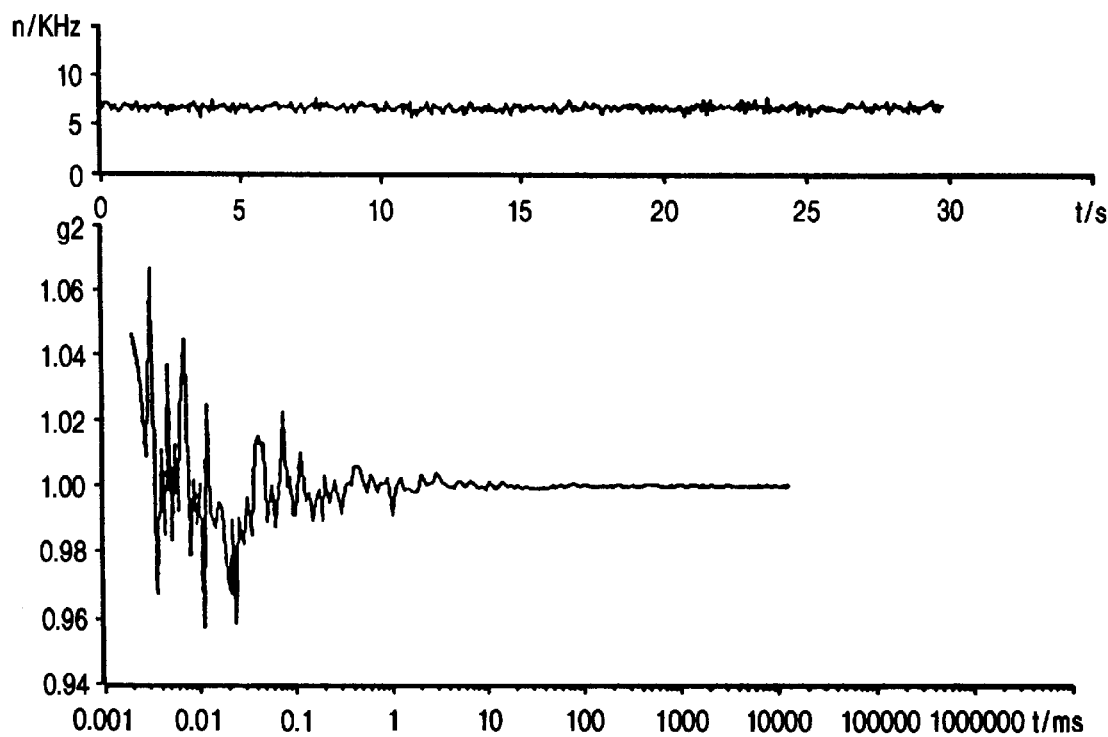
Figure 12C:
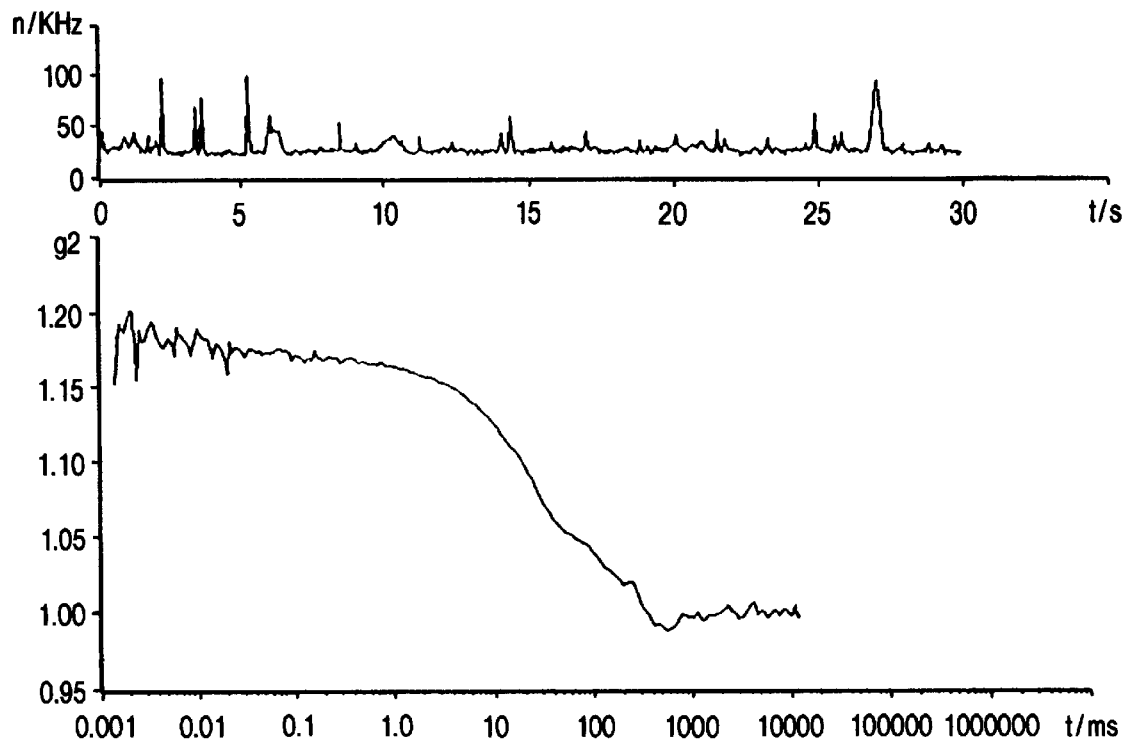
Figure 12D:
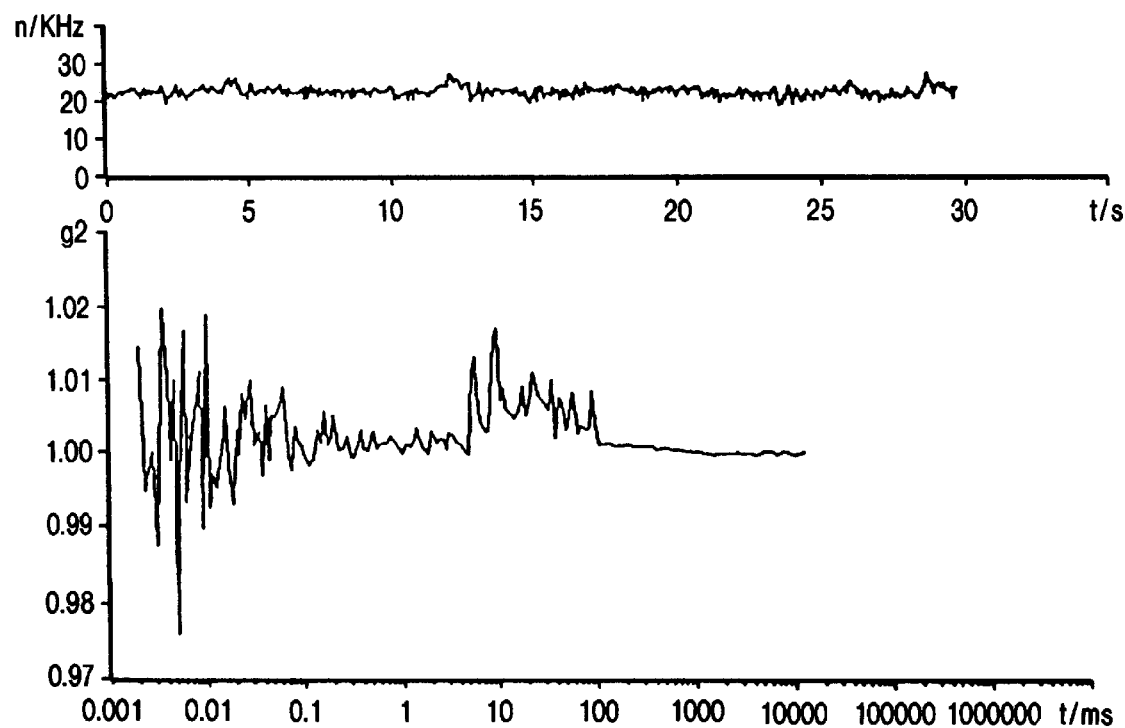
Figure 14:
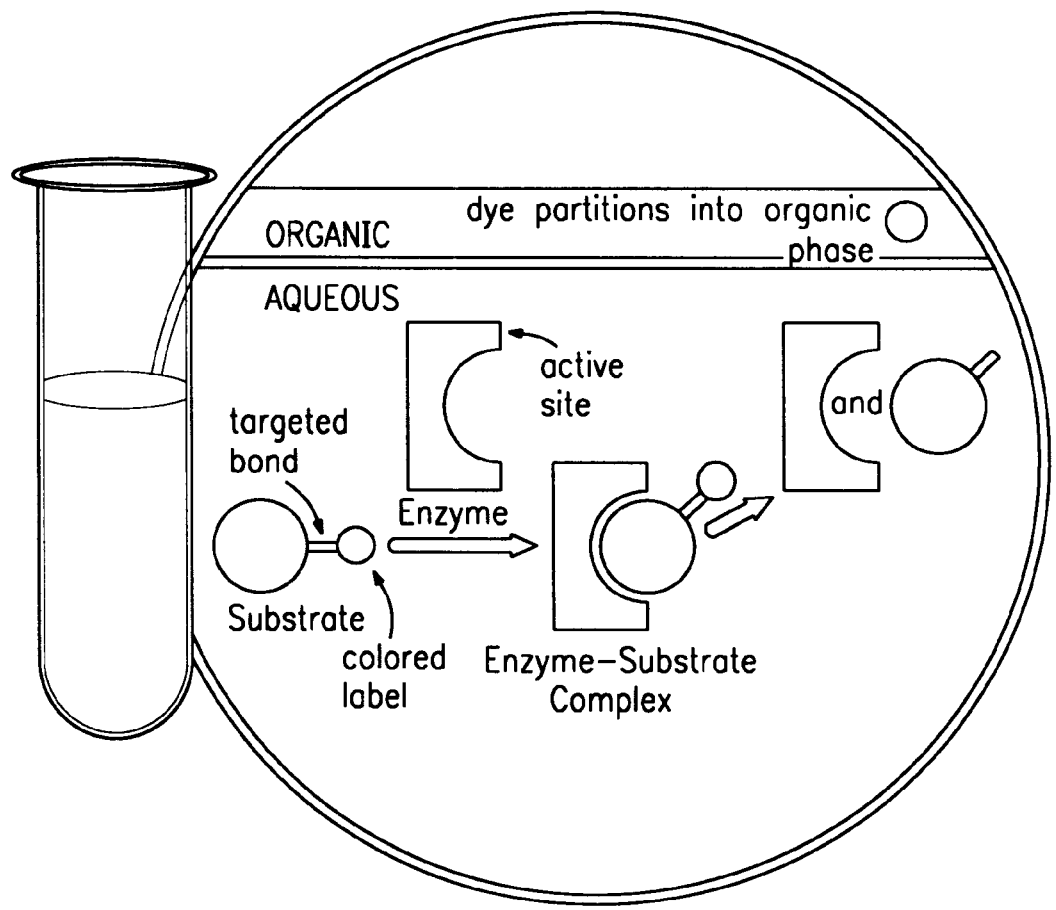
FIG. 14 illustrates the methodology being applied to screen small molecule libraries for enzyme inhibitors to HLE, caspase, and other medicinally-important proteases. The assay, while not readily apparent to the eye, is readily examined under UV light provided by a common handheld mineral lamp.
Figure 15A:
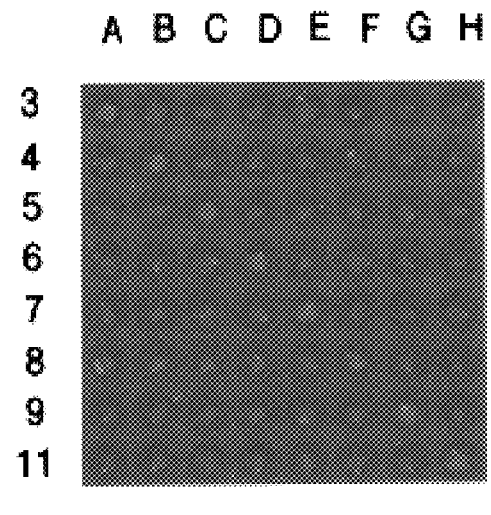
FIG. 15 shows normal light conditions and those under UV lamp. In addition, the figure depicts wells along the diagonal correspond to matching of enzyme and substrate.
Figure 15B:
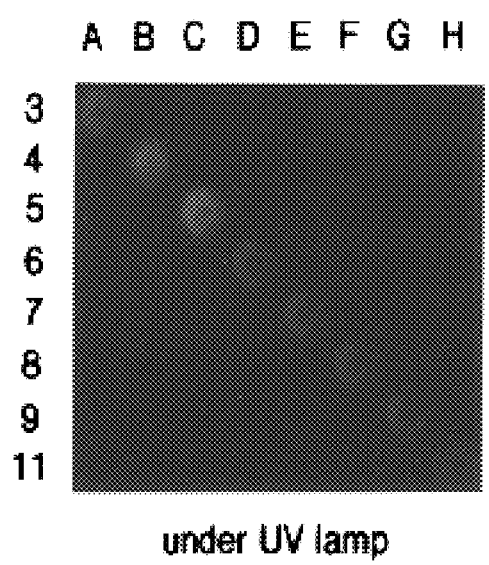

Deprotection of piperazine 900 with sulfuric acid in wet tetrahydrofuran provided a junction for attachment of a wide variety of reactive linkages. For example, the amine reactive label, SENSI—OH (100; FIG. 9), was prepared by reacting the deprotected piperazine with glutaric anhydride and then converting the terminal carboxylic acid into a N-hydroxysuccinimide ester with EDC.

The phenol can also be used as the site of linkage, as shown in SENSI (200; FIG. 9). Attachment to this site provided the advantage that this linkage could be removed hydrolytically. Synthesis of 200 was achieved by converting the t-boc protected derivative 900 into 1000, (Compound 9 was converted to 10 in order to increase the yield of further manipulations) which in turn was reacted with N-hydroxysuccimidyl glutaryl chloride to provide 200. Other linkages, such as a one carbon linked SENSIm (300), was also be prepared by the same route. All three derivatives readily reacted with bovine serum albumin (BSA) under standard conditions. Addition of 4 equivalents of SENSI—OH (100) per equivalent of BSA provided approximately 2.1 dye molecules per BSA. The efficiency of both phenol-linked derivatives 200 and 300 was much lower than that of 100, at 1.2 and 0.8 respective fluorescent units per BSA. This likely resulted from hydrolysis of the phenolic ester attachment during coupling. The conjugates of BSA with 200 and 300 were both stable between pH 5.9 and 8.1 where minimal release of the dye was visible during dialysis. The hydrolysis was determined by monitoring the loss of absorption at 400 nm after 5 hours of dialysis at the designated pH. However, considerable hydrolysis occurred outside this region, often leaving minimal label.

The spectroscopic properties of these materials was comparable to that displayed by DHNB (compound 4). For instance, the LV/visible absorption maximum of compound 1000 was red-shifted by 33 nm upon changing from n-hepane to methanol. The extinction coefficient was largest in aromatic solvents such as benzene and toluene, and also decreased with polarity. The intensity of B-band was between 14 and 63% greater than the K-band in most solvents except DMF (The assignment of K and B-bands is described by A. Burawoy, Ber. Dtsch. Chem. Ges. 1930, 63, 3155. The enhancement of the B-band was significantly greater in protic (54–63%) than in aprotic media (14–47%)). Fluorescence from 1000 shifted by =111 nm and increased 120 fold upon changing from methanol to n-hepane. The intensity of the fluorescence enhancement was 8 fold less than the parent DBNB. This may due to the fact that the piperazine ring exerts a greater tendency to conjugate with the aryl r-system, than the dimethylamino group, hence restricting its freedom to rotate to form additional fluorescence states. One possible explanation is that this is due to the lack of additional TICT states by minimization of rotation about the aryl-piperidine bond. For work describing TICT states see Grabowski et al. Nouv. J. Chim. 1979, 3, 443; Rettig, et al. Angew. Chem. 1986, 98, 969; Angew. Chem., Int. Ed. Engl. 1986, 25, 971.

As displayed in FIG. 10, single molecules from these dyes were detectable at sub-micromolar concentrations in polar solvents, such as THF, chloroform, acetone, acetonitrile, DMF, ethanol, methanol, and water using a confocal fluorescence correlation spectrometer. Single molecule studies were run on an Eigen-Rigler confocal fluorescence correlation spectrometer. All samples were excited at 457 nm (0.5 W) with an argon ion laser (Lexel, Waldbroon-Germany) which was passed through a water immersible objective (Zeiss Plan Neofluar 40x0.9) and attached to a droplet of the material through a drop of water and a hanging cover slip (Fisher 12-5454-101). The materials were contained in a 20 L gold well and were filtered through porous glass filter immediately prior to use. The fluorescence was collected through the same objective and filtered with a 545 nm cutoff filter. See: Eigen et al. Proc. Natl. Acad. Sci. USA 1994, 91, 5740; Rigler et al., J. Biotech. 1995, 41, 177.

Single molecules were detected at far lower concentrations in non-polar solvents such as n-hepane, providing a gain in response of approximately 40,000 for selective detection of single molecules.

EXAMPLE 3

A New Screening Method for Examining Enzymatic Hydrolysis by Monitoring a Concurrent Transfer of a Solvatochromic Dye Across an Oil-Water Barrier A new screening method is described which transiently examines enzymatic hydrolysis by monitoring a concurrent transfer of a solvatochromic dye across an oil-water barrier. Through appropriate choice of the dyes structure, ~$10^6$ fluorescence gain can be used to specifically detect the dye when contained in mineral oil. Combination of this fluorescence enhancement and the concentration of the dye by use of 1/200 volumetric ratio of organic to aqueous phase with hydrolysis provides highly efficient method to detect glucosidases, alkaline phosphatase as well as several proteases. Generalization of the method is provided by the incorporation of a water solublizing protecting group. This methodology is currently being applied to screen small molecule libraries for enzyme inhibitors to HLE, caspase, and other medicinally-important proteases. (see FIG. 16 for graphical representation of process). The assay, while not readily apparent to the eye, is readily examined under UV light provided by a common handheld mineral lamp. FIG. 17 shows normal light conditions and those under UV lamp. In addition, FIG. 17 shows wells along the diagonal correspond to matching of enzyme and substrate.

EXPERIMENTAL PROTOCALS

General $^1$H and $^{13}$C nmr spectra were recorded either on a Bruker AM-250, a Bruker AMX-400 or a Bruker AMX-500 spectrometer. Residual protic solvent CHCl$_3$ ($\delta_H$=7.26 ppm, $\delta_C$=77.0), d$_4$-methanol ($\delta_H$=3.30 ppm, $\delta_C$=49.0) and D$_2$O ($\delta_H$=4.80 ppm, $\delta_C$(of $\underline{C}$H$_3$CN)=1.7 ppm) or TMS ($\delta_H$=0.00 ppm) were used as internal reference. Coupling constants were measured in Hertz (Hz). HRMS were recorded using FAB method in a m-nitrobenzylalcohol (NBA) matrix doped with NaI or CsI. Infra-red spectra were recorded on a Perkin-Elmer FTIR 1620 spectrometer. Enantiomeric excess was determined by HPLC using a Daicel Chemical Industries CHIRALPAK AD column. Optical rotations were measured with an Optical Activity AA-1000 polarimeter. Melting points were taken on a Thomas Hoover capillary melting point apparatus and are uncorrected. Column chromatography was performed on Merck Kieselgel 60 (230–400 mesh). Analytical thin layer chromatography was performed using pre-coated glass-backed plates (Merck Kieselgel F$_{254}$) and visualized by cerium molybdophosphate or ninhydrin. Diethyl ether, tetrahydrofuran (THF) and toluene (PhCH$_3$) were distilled from sodium-benzophenone ketyl, dichloromethane (DCM) and acetonitrile from calcium hydride. Other solvents and reagents were purified by standard procedures if necessary. All reactions were conducted under an argon atmosphere in rigorously dried glassware and are magnetically-stirred with a Teflon-coated stir bar, unless otherwise indicated. Reagents were added to reaction vessels via a canula or dry syringe. Anhydrous tetrahydrofuran (THF) was distilled from sodium benzophenone ketyl. Methylene chloride, methanol, 1,4-dioxane and N,N-dimethylformamide (DMF) were purchased dry from Aldrich. Materials reacted under anhydrous conditions were dried extensively with toluene azeotrope prior to use. Thin layer chromatography (TLC) on Merck Silica Gel DC 60 plates was routinely used to monitor all reactions. TLC plates were developed by staining with iodine absorbed on silica gel. All Rf values were collected from runs in 33% ethyl acetate/hexane. Melting points were measured on a Büchi 520 and are uncorrected. Infrared spectra (IR) were collected on a Perkin Elmer Paragon 1000 PC FT-IR spectrometer. Samples were prepared on sodium chloride (NaCl) plates; neat or in a chloroform smear. UV-Visible and fluorescence spectra were measured on a Perkin Elmer Lambda 17 UV-Vis spectrometer, Perkin Elmer LS-5B luminescence spectrometer and a SLM-Aminco SPF-500C. 1H-NMR and 13C-NMR spectra were obtained at 300 MHz and 75 MHz, respectively, on a Bruker MSL300. Chemical shifts (d) are given in ppm and coupling constants (J) in hertz. Microanalyses were obtained from Beller microanalytisches labor (Göttingen, Germany). Standard flash chromatography was performed on Merck 9395 silica gel using a gradient from hexane to the solvent listed. Samples of 1 and 2 were recrystallized three times from spectral grade methanol at −20° C. to ensure purity.

Figure 3:
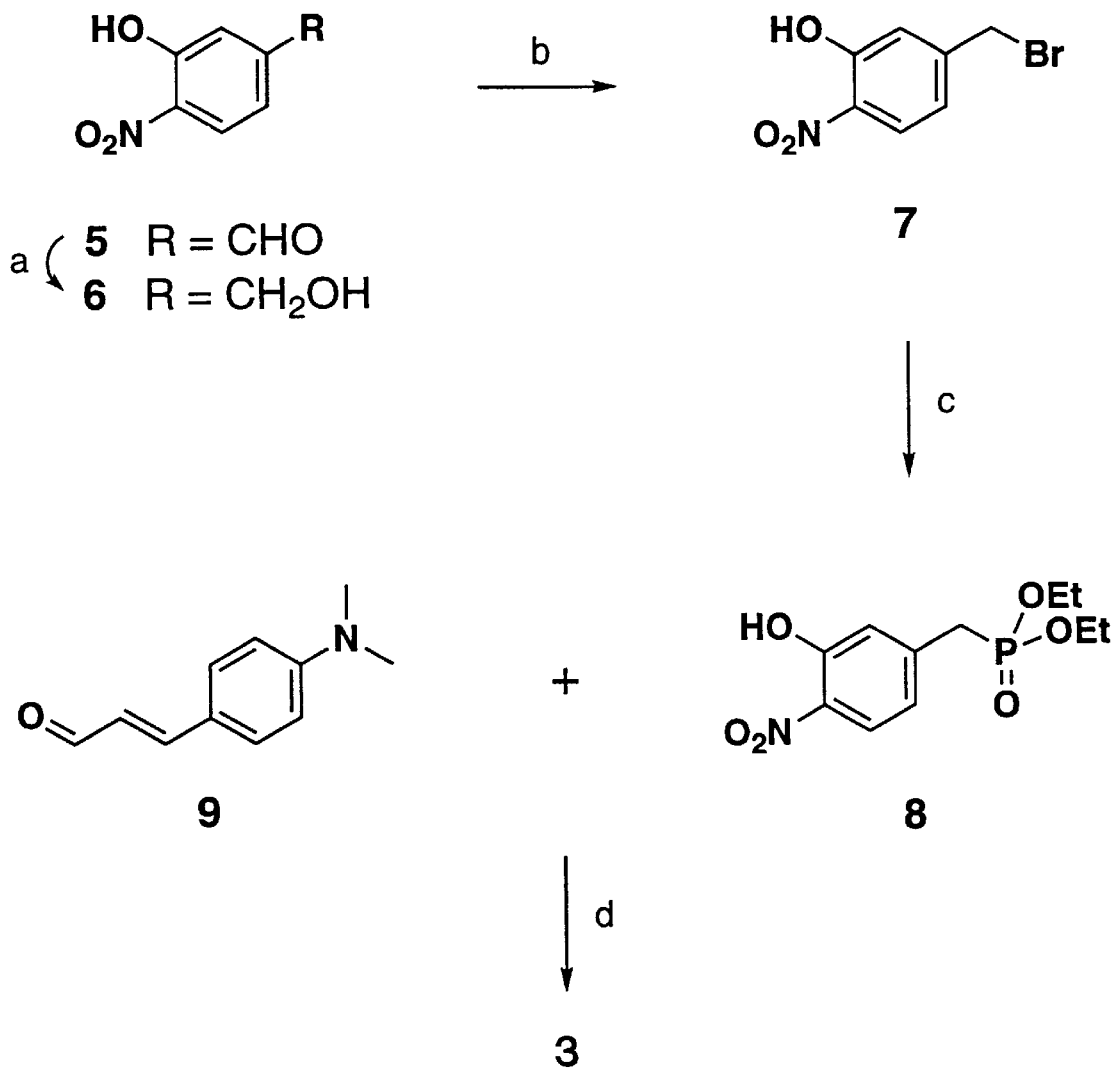
FIG. 3 shows the synthesis of 3 with the following steps: (a) $NaBH_4$, MeOH, THF, $Et_2O$ (5:5:1), 0° C. to room temperature, 97%. (b) $CBr_4$, $PPh_3$, $CH_2Cl_2$, 0° C. to room temperature, 86%. (c) $P(OEt)_3$, DMF, 155° C., 1.5 hours, 99%. (d) i. add NaHMDS (2.2 equivalents) in THF to crude 8 in DMP, 0° C. to room temperature, 1 hour; ii. add 9 in THF, −20° C. to room temperature, 6 hours, 55%.

Synthesis of m-hydroxy-p-nitrobenzyl alcohol (6) as illustrated in FIG. 3.

The synthesis of phosphonate 8 was accomplished in three operations from commercial aldehyde 5. This functional conversion began by reducing aldehyde 5 (3.74 g, 22.4 mmol) with NaBH4 (3.46 g, 91.5 mmol) in a 5:5:1 mix of methanol, ether and THF (77 mL). This was accomplished by adding NaBH4 to the solution of 5 at 0° C. over 30 min and then warming over 2 hours to room temperature. The reaction was quenched with 10% aq. HCl (until the pH was approximately 6), poured on 80 mL of brine (80 mL), extracted with 200 mL of CH$_2$Cl$_2$ (3×), dried with Na$_2$SO$_4$ and concentrated. The crude product was used directly for next step. Pure material could be obtained through flash chromatography (SiO$_2$, 50% ethyl acetate/hexanes), yielding 3.67 g (97%) of 6: mp 79.7–81.3° C.; Rf=0.37; 1H (CDCl$_3$): d 10.60 (s, 1H), 8.06 (d,J =8.8 Hz, 1H), 7.14 (s, 1H), 6.94 (d, J=8.8 Hz, 1H), 4.73 (d, J=5.5 Hz, 2H), 1.97 (t, J=5.5 Hz, 1H); 13C (CDCl$_3$): d 63.7, 116.9, 117.9, 125.2, 151.7, 155.3; IR (CHCl$_3$): 3459, 2356, 1620, 1579, 1520, 1475 cm-1. Anal. (C7H7NO4): calcd, C 49.71, H 4.17, N 8.28; found, C 50.13, H 4.30, N 8.20.

Synthesis of m-hydroxy-p-nitrobenzyl bromide (7) as illustrated in FIG. 3.

Carbon tetrabromide (2.86 g, 8.63 mmol) was added over 30 min to a solution of 6 (~1.22 g, ~7.22 mol) and PPh$_3$ (2.45 g, 9.35 mmol) in 25 mL of dry CH$_2$Cl$_2$ at 0° C. The reaction was warmed to room temperature over 1.5 hours and allowed to stand for an additional 1 hour. At which point, the mixture was poured on water, extracted with 100 mL CH$_2$Cl$_2$ (2×), dried with Na$_2$SO$_4$, and concentrated. Pure material was obtained by flash chromatography (SiO$_2$, 33% ethyl acetate/hexanes) yielding 1.42 g (86%) of 7: mp 68.9–70.2° C.; Rf=0.58; 1H (CDCl$_3$): d 10.58 (s, 1H), 8.07 (d, J=8.6 Hz, 1H), 7.16 (d, J=1.9 Hz, 1H), 6.99 (dd, J=1.9, 8.8 Hz, 1H), 4.39 (s, 2H); 13C (CDCl$_3$): d 30.6, 120.1, 120.8, 125.7, 147.8, 155.2; IR (CHCl$_3$): 2354, 1622, 1584, 1479, 1328, 1258, 1159, 968, 885, 844, 652 cm-1. Anal. (C7H6NO3Br): calcd, C 36.23, H 2.61, N 6.04; found, C 36.10, H 2.69, N 5.92.

Synthesis of Diethyl-(m-hydroxy-p-nitrobenzyl)-phosphonate (8) as illustrated in FIG. 3.

A mixture of 7 (0.91 g, 3.98 mmol) and triethylphosphite (0.87 mL, 5.09 mmol) was refluxed (bath temperature 155° C.) in 2.5 mL of dry DMF for 1.5 hours. Pure material was obtained through flash chromatography (SiO$_2$, 25% ethyl acetate/hexanes), yielding 1.14 g (99%) of 8: mp 59.3–62.1° C., Rf=0.09; 1H (CDCl$_3$): d 10.56 (s, 1H), 8.01 (d, J=8.7 Hz, 1H), 7.04 (dd, J=2.2 Hz, JH-P=2.2 Hz, 1H), 6.91 (dd, J=2.2, 8.7 Hz, JH-P=2.2 Hz, 1H), 4.04 (qd J=7.1 Hz, JH-P=8.1 Hz, 2H), 3.04 (d, JH-P=22.5 Hz, 2H), 1.25 (q, J=7.1 Hz, 3H); 13C (CDCl$_3$): d 16.2 (d, JC-P=5.3 Hz), 34.2 (d, JC-P=136.7 Hz), 62.4 (d, JC-P =6.5 Hz), 120.7 (d, JC-P=8.3 Hz), 121.8 (d, JC-P=6.0 Hz), 125.0 (d, JC-P=2.4 Hz), 143.2 (d, JCP=8.8 Hz), 154.9 (d, JCP=3.8 Hz); IR (CHCl$_3$): 3850, 3444, 2985, 1623, 1587, 1520, 1480, 1443 cm-1. Anal. (C11H16NO6P): calcd, C 45.68, H 5.58, N 4.84; found, C 45.60, H 5.74, N 4.83.

Synthesis of p-(N,N-dimethylamino)-m'-hydroxy-p'-nitro-trans-trans-1,4-diphenyl-1,3-butadiene (3) as illustrated in FIG. 3.

Sodium bis-(trimethylsilyl)amide (0.99 mL, 1.0 M in THF) was added to the crude solution of phosphonate 8 (143.6 mg, 0.453 mmol in 0.8 mL of DMF) from the above step at 0° C. Thirty min later, the solution was warmed to room temperature and kept there for 20 min. At which point, the contents were recooled to −20° C. and reacted with a solution of N,N-dimethylaminocinnamaldehyde (74.2 mg, 0.430 mmol) in 4 mL of THF. After 8 hours at ambient temperature, 15 mL of ice cold brine was added. The pH was adjusted to 7 with dilute HCl and the crude product was obtained by repetitive extraction with 10% THF in CH$_2$Cl$_2$, drying with Na$_2$SO$_4$ and concentration. Flash chromatography (33% CHCl$_3$/hexane) and recrystallization from 10:1 heptane/THF provided 302.7 mg (55 %) of 3: mp 216.3–217.2° C.; Rf=0.43; (CDCl$_3$): d 10.74 (s, 1H), 7.99 (d, J=8.7 Hz, 1H), 7.24 (d, J =8.7 Hz, 2H), 7.08 (dd, J=7.8, 15.5 Hz, 1H), 7.03 (dd, J=7.8, 16.9 Hz, 1H), 7.02 (d, J=16.9 Hz, 1H), 6.75 (d, J=7.8 Hz, 2H), 6.74 (s, 1H), 6.65 (d, J=8.7 Hz, 2H), 6.47 (d, J=15.4 Hz, 1H), 2.98 (s, 6H); 13C—NMR (d6-DMSO): d 30.6, 112.3, 115.9, 117.0, 124.1, 124.6, 125.8, 127.4, 128.0, 133.9, 135.2, 136.7, 145.6, 150.6, 153.6; IR (trace CHCl$_3$): 3850, 3741, 2357, 2169, 1574, 1470, 1219, 962, 944, 772, 674 cm-1. Elemental analysis (C18H18N2O3): calculated, C 69.66, H 5.85, N 9.03; found, C 69.72, H 5.97, N 9.06.

Synthesis of N,N-Dimethyl-p-iodoaniline (11) as illustrated in FIG. 4.

Resublimed iodine (4.28 g, 16.8 mmol) was added in small portions over 45 min to a mixture of N,N-dimethylaniline (10) (2.37 mL, 18.7 mmol) and NaHCO$_3$ (2.35 g, 27.9 mmol) in 16 mL of water between 12 and 15° C. Ten minutes after complete addition, the mixture was warmed to room temperature. This mixture was diluted with 500 mL of ether and the organic phase extracted consecutively with 50 mL of water, 100 mL of sodium thiosulfate and 100 mL of water (2×). Afterwards, the crude product was dried with Na$_2$SO$_4$, concentrated and recrystallized from 10:1 hexane/ether to yield 3.98 g (86%) of 11: mp 63.5–66.1° C.; Rf=0.66; 1H (CDCl$_3$): d 7.45 (d, J=8.9 Hz, 2H), 6.46 (d, J=8.9 Hz, 2H), 2.90 (s, 6H); 13C (CDCl$_3$): d 40.2, 114.8, 137.3, 149.9.

p-(N,N-dimethylamino)-3-phenylpropynol (12).

A mixture of iodide 11 (309.7 mg, 1.25 mmol), Cl$_2$Pd (PPh$_3$)2 (6.4 mg, 0.0091 mmol) and CuI (9.5 mg, 0.0499 mmol) in 1.2 mL of triethylamine was degassed by a rapid bubbling of argon. After 30 min, 2-propyn-1-ol (0.087 mL, 1.37 mmol) was added via microliter syringe. Three hours later, a second batch of Cl$_2$Pd(PPh$_3$)2 (6.4 mg) and CuI (9.5 mg) was added and the reaction went to completion within 18 hours. A strict maintenance of an argon atmosphere was crucial to the yield of this manipulation. The crude solution was filtered through 20 g of silica gel with ethyl acetate and concentrated. Pure material was obtained through flash chromatography (SiO$_2$, 25% ethyl acetate/hexanes), yielding 195.2 mg (89%) of 12: mp 51.2–53.7° C.; Rf=0.31; 1H (CDCl$_3$): d 7.30 (d, J=8.9 Hz, 2H), 6.60 (d, J=8.9 Hz, 2H), 4.45 (d, J=4.1 Hz, 2H), 2.95 (s, 6H); 13C (CDCl$_3$): d 40.1, 51.8, 85.1, 88.7, 109.5, 111.8, 132.8, 150.3; IR (trace CHCl$_3$): 3355, 2860, 1608, 1520, 1445, 1360, 1225, 1190, 1024, 955, 818 cm-1. Anal. (C11H13NO): calcd, C 75.40, H 7.48, N 7.99; found, C 75.33, H 7.42, N 7.96.

Synthesis of p-(N,N-dimethylamino)-3-phenylpropynal (13) as illustrated in FIG. 4.

Activated MnO$_2$ (1.148 g, 13.2 mmol) was added to a solution of 12 (421.5 mg, 2.41 mol) in 10 mL of CH$_2$Cl$_2$ at room temperature. After 4 hours, the reaction directly purified by flash chromatography (SiO$_2$, 25% ethyl acetate/ hexanes), yielding 371.8 mg (89%) of 13: mp 81.4–82.3° C.; Rf=0.49; 1H (CDCl$_3$): d 9.33 (s, 1H), 7.44 (d, J=9.0 Hz, 2H), 6.60 (d, J =9.0 Hz, 2H), 3.01 (s, 6H); 13C (CDCl$_3$): d 39.8, 96.0, 99.9, 104.9, 111.5, 135.2, 152.1, 176.2; IR (trace CHCl$_3$): 2149, 1643, 1595, 1380, 1190, 981 cm-1. Anal. (C11H11NO): calcd, C 76.28, H 6.40, N 8.09; found, C 76.42, H 6.41, N 8.07. Alternatively, large scale preparations can be purified by recrystallization from 20:1 heptane/THF.

Synthesis of p-(N,N-dimethylaminio)-p'-nitro-trans-1,4-diphenyl-1-buten-3-yne (4) as illustrated in FIG. 4.

Sodium bis-(trimethylsilyl)amide (6.27 mL, 1.0 M in THF, 6.27 mmol) was added to the crude solution of the phosphonate 8 (~852.0 mg, ~2.95 mmol) in 2.0 mL of DMF at 0° C. A dramatic color change (light yellow to deep magenta) occurred upon exceeding the first equivalent of base. This internal standardization was routinely used to ensure proper addition of base. The solution was warmed to room temperature after 30 min at 0° C. and kept there for 20 min. At which point, it was cooled to −20° C. and aldehyde 6 (310.0 mg, 1.79 mmol) in 5 mL of THF was added via canula. After 8 hours at room temperature, 5 mL of water was added, the pH was adjusted to 7 with dilute HCl and then further diluted with 10 mL brine. Crude product was obtained by extraction with 40 mL 10% THF in CH$_2$Cl$_2$ (3×), dried with Na$_2$SO$_4$, and concentrated. Flash chromatography (SiO$_2$, 33% CHCl$_3$/hexanes) and recrystallization from heptane/THF (10:1) yielded 308.2 mg (56%) of 4 mp 185.6–186.9° C.; Rf=0.28; 1H (CDCl$_3$): d 10.65 (s, 1H), 8.02 (d, J=8.8 Hz, 1H), 7.34 (d, J=8.9 Hz, 2H), 7.07 (d, J=1.6 Hz, 1H), 6.99 (dd J=1.6, 8.9 Hz, 1H), 6.84 (d, J=16.0 Hz, 1H), 6.62 (d, J=8.9 Hz, 2H), 6.55 (d, J=16.0 Hz, 2H), 2.98 (s, 6H); 13C (d6-DMSO): d 39.6, 87.4, 96.6, 108.9, 111.2, 113.8, 116.6, 117.0, 125.7, 132.6, 135.2, 136.8, 143.7, 150.5, 153.1; IR (trace CHCl$_3$): 3850, 3741, 2357, 2169, 1574, 1470, 1219, 962, 944, 772, 674 cm-1. Anal. (C18H16N2O3): calcd, C 70.12, H 5.23, N 9.09; found, C 70.22, H 5.49, N 9.07.

Synthesis of Glucopyranoside 2 as illustrated in FIG. 4.

N-Benzyltriethylammonium chloride (254.8 mg, 1.12 mmol) was added to a suspension of 4 (345.1 mg, 1.12 mmol) and 2,3,4,6-tetraacetoxy-a-D-glucopyranosylbromide (922.0 mg, 2.24 mmol)in 4 mL of CH$_2$Cl$_2$ and 10 mL of 1 M NaOH. After 12 hours, the reaction mixture was diluted with 100 mL ethyl acetate and 20 mL of water and extracted. The aqueous phase was further extracted with 50 mL of ethyl acetate (2×) and the combined organic layers were washed with 10 mL of water (2×). Crude material was obtained by drying with Na$_2$SO$_4$ and concentrating. This material was dissolved in 10 mL of methanol and 6 mL of benzene and treated with 0.25 mL of 1 M NaOCH$_3$ in methanol. After 1 hour, 330 mg of benzoic acid was added followed by 1.2 g of NaHCO$_3$, 15 minutes later. The residual NaHCO$_3$ was filtered off and the excess methanol was removed by rotary evaporation. Flash chromatography (SiO$_2$, 10:1:1 ethyl acetate/methanol/toluene) and recrystallization from methanol to afford 510.2 mg (86%) of 1:1 mixture of 2 and its benzoate salt. The pure amine was obtained by heating this material for 2 hours in dry 1,4-dioxane containing 1.3 g of 4 Å molecular sieves. The crude material was obtained by filtration aided by extensive washing with methanol and concentration. Flash chromatography (SiO$_2$, 10:1:1 ethyl acetate/methanol/toluene) and recrystallization from methanol (3×) yielded 375.2 mg (71%) of pure 2; mp=177.9–182.5° C.; Rf=0.28 (10:1:1 ethyl acetate/methanol/toluene); 1H (CDCl$_3$): d 7.72 (d, J=8.4 Hz, 1H), 7.44 (d, J=1.4 Hz, 2), 7.20 (d, J=8.7 Hz, 1H), 7.17 (dd J=1.4, 8.4 Hz, 1H), 6.85 (d, J=16.2 Hz, 1H), 6.62 (d, J=8.7 Hz, 2H), 6.60 (d, J=16.0 Hz, 2H), 5.03 (d, J=7.3 Hz, 2H), 3.86 (dd, J =2.1, 12.0 Hz, 2H), 3.67–3.57 (m, 2H), 3.50–3.37 (m, 3H), 3.28–3.22 (m, 1H), 2.90 (s, 6H); 13C (CD3OD): d 40.6, 63.1, 71.8, 75.2, 78.4, 79.0, 88.0, 97.4, 103.2, 111.4, 113.4, 115.1, 116.5, 121.1, 127.0, 134.0, 139.1, 144.7, 152.4; Hi Res MS (FAB) (C24H26N208): found, 470.1689; found, 470.1699.

Synthesis of Maltopyranoside 1 as illustrated in FIG. 4.

A saturated solution of HBr in HOAc (1.5 mL) was added to a 18:1 mixture of b: a per-acetylated maltose in 0.4 mL of HOAc at 0° C. The mixture was warmed to 15° C. over 30 min and kept there for an additional 30 min. At which point it was concentrated to dryness by warming to 40° C. at 10 mm Hg (generated by water aspirator pump). N-Benzyltriethylammonium chloride (106.0 mg, 0.32 mmol) was added to a suspension of 4 (0.0987 mg, 0.32 mmol) and the above maltopyranosylbromide (891.0 mg, 1.27 mmol) in 8 mL of CH$_2$Cl$_2$ and 8 mL of 1 M NaOH. After 12 hours, the reaction mixture was diluted with 4 mL of cyclohexane and filtered. The filter paper was dried and washed extensively with methanol (~100 mL) and concentrated to 80 mL. This solution was treated with 1.2 mL of 1 M methanolic solution of NaOCH$_3$ for 1 hour. The reaction was buffered by addition of 380 mg of benzoic acid. The crude product was obtained by filtering, washing extensively with methanol and concentrating. Flash chromatography (SiO$_2$, 10:1:1 ethyl acetate/methanol/toluene to methanol) and recrystallization from methanol yielded the benzoate salt of 1. The pure amine was obtained by heating the above material for 2 hours in 5 mL of dry 1,4-dioxane containing 0.8 g of 4 Å molecular sieves. The crude material was obtained by filtration aided by extensive washing with methanol and concentration. Recrystallization from methanol (3×) yielded 139.7 mg (69%) of pure 1; mp=229.2–232.7° C.; Rf=0.54 (CH$_3$OH); 1H (CDCl$_3$): d 7.72 (d, J=8.6 Hz, 1H), 7.42 (d, J=1.2 Hz, 2H), 7.20 (d, J=8.7 Hz, 1H), 7.17 (dd J=1.2, 8.6 Hz, 1H), 6.66 (d, J=16.2 Hz, 1H), 6.62 (d, J=8.7 Hz, 2H), 6.60 (d, J=16.2 Hz, 2H), 5.13 (d, J=3.7 Hz, 2H), 5.07 (d, J=7.6 Hz, 2H), 3.88 (dd, J=12.2 Hz, 2H), 3.79–3.41 (m, 8H), 3.37 (dd, J=3.7, 9.7 Hz, 1H), 3.35–3.21 (m, 2H), 2.90 (s, 6H); 13C (d6-DMSO): d 39.6, 61.5, 62.4, 67.1, 67.7, 71.2, 73.5, 73.6, 74.0, 74.4, 76.6, 77.0, 80.5, 87.3, 101.8, 102.1, 112.3, 113.9, 115.1, 120.2, 125.5, 125.8, 128.9, 129.9, 132.9, 133.1, 137.1, 143.2; Anal. (C30H36N2O13): calcd, C 56.96, H 5.74, N 4.43 found, C 56.89, H 5.62, N 4.41.

Absorption and Fluorescence Measurements.

Samples of 1 and 2 were prepared by dissolving between 0.2–3.8 mg in a 5 mL volumetric flask using the appropriate solvent. Absorption spectra were run in quartz cuvettes with a width of 0.5 cm. Fluorescence intensities were compared at a standard concentration of 10 mM and the quantum yields were standardized against 0.70 for Rhodamine B in ethanol. A list of the absorption maxima, extinction coefficients, fluorescence maxima and quantum yields provided is an average of three repetitions of the above, the data deviated within 4%. Several samples were diluted by 10 fold (to 1 mM) and their fluorescence spectrum retaken to ensure that the data was not enhanced by aggregation.

Concanavalin A Binding Experiments-data shown in FIG. 6 (General procedure).

Concanavalin A, type VI, was purchased from Sigma (Lot 105H9567) and used as is. Water used for FCS studies was distilled twice following deionization. MnCl$_2$ and CaCl$_2$ were purchased from Sigma, molecular biology grade. Buffer was prepared with 0.05 M PIPES (pH 7.2), 10 mM MnCl$_2$, 10 mM CaCl$_2$, and 1 M NaCl. Stock solutions of glucosides 1 and 2 were prepared at 0.24 mM and 0.12 mM in above buffer by first dissolving in 100 mL of ethanol and then diluting with buffer to 10 mL. These samples were warmed to 45° C. prior to usage to ensure complete solvation. A 0.5 mM stock solution of Con A was prepared in each buffer and verified by comparison to the reported e=1.14 cm2/mg at 280 nm. Samples were filtered through Cameo 25 GAS syringe filter immediately prior to use to remove any interfering particles. Stability of Con A to the conditions was verified by electrophoresis upon completion of the measurements.

FCS studies were conducted by excitation with the 457 nm line of an argon laser (Lexel Argon Ion, Waldbroon-Germany) at 0.5 mW which was focused through a water-immersion microscope objective (Zeiss Plan Neofluar 40×0.9) providing a volume element of approximately 2×10$^{-16}$. Fluorescent molecules were excited for 0.1–50 ms as they passed through this volume element, as given by diffusion coefficients. The fluorescence was collected by the same objective, light scattering was blocked with a dichroic mirror, and passed through a 545 cutoff filter (Omega Optics) and a pinhole in image space. Fluorescence was detected by a SPAD (EG & G-Chemie, Steinheim-Germany) and signal autocorrelation was carried out by PC with a digital autocorrelator card (ALV-5000 Fa. Peters, Langen-Germany). Samples containing 51 mM 1 and 12 mM 2 were prepared with a gradient of Con A from 0, 0.5, 5.0 mM, 50 mM to 170 mM. These samples were stored at room temperature for 12 hours prior to measurement. A single droplet of these solutions (~20 mL) was hung from fresh microscope slides and its fluorescence observed over 30 seconds. Repetition with three different preparations provided intensities of fluctuation within 3% of the original run. Signals due to aggregates were detected in a solution with 50 mM 1 and 170 mM Con A. Signals were not detected in samples of 2 with 170 mM Con A as well as in the presence of 1 mM Con A.

Synthesis of 400 as illustrated in FIG. 8:

Di-tert-butyl dicarbonate (4.5 g, 20.6 mmol) was added in small portions over 15 min to a mixture of N-phenylpiperazine (3.0 mL, 19.6 mmol; Aldrich), triethylamine (8.2 mL, 58.9 mmol), and DMAP (86 mg) in 100 mL of dry CH$_2$Cl$_2$ at 0° C. Ten minutes after complete addition, the mixture was warmed to room temperature. After 1.5 hours, it was diluted with 200 mL of CH$_2$Cl$_2$ and 100 mL of water and extracted. The aqueous phase was further extracted with two additional 100 mL portions of CH$_2$Cl$_2$, washed with brine, dried with Na$_2$SO$_4$, concentrated to yield 4.87 g (94%) of 400.

Synthesis of 500 as illustrated in FIG. 8:

Iodine (5.0 g, 19.7 mmol) was added over 45 min to 400 (5.46 g, 20.8 mmol) and NaHCO$_3$ (2.62 g, 31.2 mmol) in 80 mL of CH$_2$Cl$_2$ and 60 mL of water which was kept between 12 and 15° C. After the addition was complete, the mixture was warmed to room temperature and kept there for 30 min. The mixture was then diluted with 500 mL of $CH_2Cl_2$ and 100 mL of water, the organic phase was collected and consecutively washed with 50 mL of water, 100 mL of sodium thiosulfate, 100 mL of water (2×), and 100 mL of brine. The crude product was dried with $Na_2SO_4$, concentrated and recrystallized from 10:1 n-hexane/THF to yield 6.95 g (90%) of 500.

Synthesis of Compound 600 as illustrated in FIG. 8.

A mixture of iodide 500 (1.17 g, 3.02 mmol), $_{Cl2}Pd(PPh_3)_2$ (21.2 mg, 0.032 mmol) and CuI (5.7 mg, 0.032 mmol) in 2 mL of THF and 5 mL of triethylarnine was degassed by rapid bubbling of dry argon. After 15 min of degassing, 2-propyn-1-ol (0.193 mL, 3.32 mmol) was added to the vigorously stirred mixture. Three hours later, a second batch of $Cl_2Pd(PPh_3)2$ and CuI was added and the reaction went to completion within 18 hours. A strict maintenance of an argon atmosphere was crucial to the yield of this manipulation. The crude solution was filtered through 30 g of silica gel with 5% methanol in ethyl acetate and concentrated. Pure material was obtained through flash chromatography ($SiO_2$, 25% ethyl acetate/hoursexanes), yielding 815.2 mg (85%) of 600.

Synthesis of Compound 700 as illustrated in FIG. 8.

Activated $MnO_2$ (0.507 g, 5.83 mmol) was added to 600 (615.0 mg, 1.94 mol) in 18 mL of $CH_2Cl_2$ at room temperature. After 6 hours, the reaction directly purified by flash chromatography ($SiO_2$, 25% ethyl acetate/hexanes), yielding 602.1 mg (98%) of 700.

Synthesis of Compound 900 as illustrated in FIG. 8.

Sodium bis-(trimethylsilyl)amide (4.79 mL, 1.0 M in THF, 4.79 mmol) was added to phosphonate 8 (~621 mg, ~2.15 mmol; synthesized above) in 6.0 mL of DMF at 0° C. The solution was warmed to room temperature after 30 min at 0° C. and kept there for 20 min. At which point, it was recooled to −20° C. and aldehyde 700 (376.5 mg, 1.19 mmol) in 10 mL of THF was added via canula. After 8 hours at room temperature, 5 mL of water was added, the pH was adjusted to 7 with 5% aqueous HCl and then further diluted with 10 mL brine. Crude product was obtained by extraction with 40 mL of 10% THF in $CH_2Cl_2$ (3×), dried with $Na_2SO_4$, and concentrated. Flash chromatography ($SiO_2$, 33% $CHCl_3$/hexanes) and recrystallization from n-hepanen/THF (10:1) yielded 331.4 mg (62%) of 900.

Synthesis of SENSI-OH (100) as illustrated in FIG. 9:

Concentrated sulfuric acid (130 l) was added to 900 (82.1 mg, 0.178 mmol) in 9 mL of 10% aqueous THF at 0° C. After 20 min, aqueous satd. sodium bicarbonate solution was added until pH 6.5, followed by 15 mL of brine. The crude product was obtained by extraction with 10% THF in $CH_2Cl_2$ (3×60 mL), dried with $Na_2SO_4$, and concentrated. This isolate was treated with glutaric anhydride (26.4 mg, 0.231 mmol) and DMAP (~3 mg) in 8 mL of dry THF. After 2 hours at room temperature, N-hydroxysuccinimide (40.9 mg, 0.356 mol) was added followed by EDC (119.4 g, 0.623 mmol). Twelve hoursours later, 10 InL of water was added, the pH adjusted to 6.5 with dilute HCl and followed by extraction with 10% THF in $CH_2Cl_2$ (3×80 mL), drying with $Na_2SO_4$, and evaporation. Recrystallization from a 2.5:1 mixture of n-hepane and THF provided 80.7 mg (81%) of pure 100.

Synthesis of SENSI (1000) as illustrated in FIG. 9:

Concentrated sulfuric acid (80 l) was added to 900 (49.5 g, 0.107 mmol) in 5 mL of 10% aqueous THF at 0° C. After 20 min, aqueous satd. sodium bicarbonate solution was added until pH 7.0, followed by 10 mL of brine. The crude product was obtained by extraction with 10% THF in $CH_2Cl_2$ (3×40 mL), dried with $Na_2SO_4$, and concentrated. This isolate was immediately dissolved in dry THF (5 mL) and treated with glutaric anhydride (14.6 mg, 0.128 mmol) and DMAP (~2 mg). After 2 hours at room temperature, dry methanol (0.2 mL) was added followed by EDC (61.7 g, 0.321 mmol). The esterification was complete after 4 hours as indicated by TLC. At which point, 10 mL of water was added and the product isolated by adjustment of the pH to 6.5 with dilute HCl followed by extraction with 10% THF in $CH_2Cl_2$ (3×40 mL), drying with $Na_2SO_4$, and rotary evaporation. Pure material was obtained by recrystallization from a 3:1 mixture of n-hexane and THF, yielding 39.2 mg (77%) of 1000.

Synthesis of compound 200 as illustrated in FIG. 9.

N-Hydroxysuccimidyl glutaryl chloride (81.1 mg, 0.327 mmol) was added to compound 1000 (41.9 mg, 0.0953 mmol) and DMAP (~1 mg) in 5 mL of dry THF. After 12 hours at room temperature, 10 mL of water was added and the product isolated by adjustment of the pH to 6.5 with dilute HCl followed by extraction with 10% THF in $CH_2Cl_2$ (3×30 mL), drying with $Na_2SO_4$, and rotary evaporation. Pure material was obtained by recrystallization from a 3:1 mixture of n-hepane and THF, yielding 40.9 mg (64%) of 200.

Synthesis of compound 300 as illustrated in FIG. 9.

N,N-carbonyldimidazole (81.1 mg, 0.327 mmol) was added to compound 1000 (41.9 mg, 0.0953 mmol) and DMAP (~1 mg) in 5 mL of dry THF. After 12 hours at room temperature, 10 mL of water was added and the product isolated by adjustment of the pH to 6.5 with dilute HCl followed by extraction with 10% THF in $CH_2Cl_2$ (3×30 mL), drying with $Na_2SO_4$, and rotary evaporation. Pure material was obtained by recrystallization from a 3:1 mixture of n-hepane and THF, yielding 40.9 mg (64%) of 200.

General coupling with BSA:

The bovine serum albumin (BSA) used in these studies was purchased from Sigma, product A 7030. SENSI-OH (100) (alternatively SENSI 200 300 or 1000 are coupled using these identical conditions) (1.2 mg, 2.14 mol) in 50 L of DMF was added in five portions to BSA (35.9 mg, 0.54 mol) in 5 mL of PBS buffer. The mixture was allowed to react for 8 hours at room temperature. Upon completion this material was diluted with 5 mL of water, dialyzed (Spectra/por MWCO 12,000–14,000) extensively against water and lyophilized dry. The absorption spectrum was collected on a small portion of this material (2–3 mg) which was dissolved in 500 l of PBS. The approximate number of fluorophores per protein was the calculated based on the known absorption of 100 in PBS and the concentration of labeled BSA.

General procedure for the attachment of Dye molecules to the carbohydrate molecules.

N-Benzyltriethylammonium chloride (254.8 mg, 1.12 mmol) is added to a suspension of Dye compound 4, 900, 1000, 100, 200 or 300 (345.1 mg, 1.12 mmol) and carbohydrate (922.0 mg, 2.24 mmol; a carbohydrate covers all commercially available simple sugars, mono, di- tetra saccharides and polysaccharide polymers such as cellulose, starch, etc.) in 4 mL of $CH_2Cl_2$ and 10 mL of 1 M NaOH. After 12 hours, the reaction mixture is diluted with 100 mL ethyl acetate and 20 mL of water and extracted. The aqueous phase was further extracted with 50 mL of ethyl acetate (2×) and the combined organic layers were washed with 10 mL of water (2×). Crude material iss obtained by drying with $Na_2SO_4$ and concentrating. This material is dissolved in 10 mL of methanol and 6 mL of benzene and treated with 0.25 mL of 1 M $NaOCH_3$ in methanol. After 1 hour, 330 mg of benzoic acid is added followed by 1.2 g of $NaHCO_3$, 15 minutes later. The residual NaHCO₃ is filtered off and the excess methanol is removed by rotary evaporation. Flash chromatography (SiO₂, 10:1:1 ethyl acetate/methanol/toluene) and recrystallization from methanol to afford salt. If possible, the pure amine is obtained by heating this material for 2 hours in dry 1,4-dioxane containing 1.3 g of 4 Å molecular sieves. The crude material is obtained by filtration aided by extensive washing with methanol and concentration. Flash chromatography (SiO₂, 10:1:1 ethyl acetate/methanol/toluene) and recrystallization from methanol (3×) yields conjugate.

General procedure for the attachment of Dye molecules to the peptide molecules or protein molecules Method A: A mixture of desired Dye compound 4, 900, 1000, 100, 200 or 300 disclosed herein (1.5 equivalents), Peptide-NH₂ or Protein-NH₂ (1 equivalent; Aldrich/Sigma/Fluka, etc.; any commercially or readily available protein with free amino functionalities—alternatively Peptide-COOH or Protein-COOH can be used with a free amine derivative of the dye molecule), N,N-dimethylaminopyridine (DMAP, 0.0231 g, 0.189 mmol, 0.25 equivalents) and 1,3-dicyclohexylcarbodiimide (DCC, 0.233 g, 1.13 mmol, 1.5 equivalents) in methylene chloride (DCM) was stirred overnight at room temperature. After the reaction was complete, the insoluble urea side-product was removed by filtration and the conjugated dye/peptide (4.34 g, 98%) was isolated from the reaction mixture by precipitation following a slow addition of diethyl ether or other medium known to precipate known peptide or protein.

Method B: Dye compound 4, 900, 1000, 100, 200 or 300 (1–1.5 equivalents) was suspended in 0.10 Molar DMF at 0° C. Next, 1.1 equivalents sufosuccinimide (Aldrich) and 1.1 equivalents EDC (1–3-Dimethylaminopropyl)-3-ethyl-carbo-diimide-hydrochloride Aldrich) were added and the mixture was stirred for 2 hours at 25° C. Next, either 1.1 equivalents KLH (keyhole limpet hemacyanin; Sigma) or 1.1 equivalents BSA (bovine serum albumin; Sigma-these proteins are included for example-other commercially available peptides/proteins include but are not limited to insulins, neurokinins, leucokinins, fibronectins, calmodulin, kinases etc.—See pages 1076–1081 of 1996 Sigma Catalog for listing of available peptides/proteins to be conjugated with the dye) was added and the mixture was stirred at 25° C. for 12 hours. The mixture was next quenched with successive saturated solution washes of ammonium chloride, water and dried over magnesium sulfate. The compound was purified via reverse phase BPLC to afford dye-conjugated protein.

There are many different carrier proteins which can be used for coupling to dye molecules. The two most commonly used carrier proteins are keyhole limpet hemacyanin (KLH) and bovine serum albumin (BSA). Both of these proteins work well, but each has disadvantages. KLH, due to its large size, can precipitate during cross-linking which makes handling difficult in some cases. BSA is very soluble but is often an immunogen in its own right. BSA has 59 lysine (30–35 are available for coupling), 19 tyrosine, 35 cystein, 59 glutamic acid and 39 aspartic acid residues.

Other carriers, which are used, include ovalbumin, mouse serum albumin and rabbit serum albumin. Ovalbumin can be successfully used in most cases and is a reasonable choice to be used as a second carrier when checking for antibody specificity to the peptide itself and not the carrier protein. Mouse serum albumin (MSA) and rabbit serum albumin (RSA) can be used when the antibody response to the carrier molecule must be kept to a minimum.

General procedure for the attachment of Dye molecules to the nucleic acid molecules:

If desired nucleic acids are not commercially available for tagging with dye compounds 4, 900, 1000, 100, 200 or 300 (1–1.5 equivalents), than they are synthesized according to the following procedure, wherein, all monomers, reagents and solvents for DNA synthesis can be purchased from Applied Biosystem (ABI) or Glen Research unless otherwise indicated. Expedite β-cyanoethyl phosphoramidites (Millipore) are protected with t-butylphenoxyacetyl on the amino groups of Adenine, Guanine, and Cytidine; Thymidine is not protected; the phosphate backbone generated with these monomers is protected as β-cyanoethyl ester. The phosphoramidite monomers used with a few of the second generation cassettes require incubation in concentrated ammonia in a sealed tube at 55° C. for 16–20 hours. In order to minimize this exposure we used Expedite phosphoramidites with most of the reaction cassettes which allowed for rapid deprotection (1 hour at 55° C. in concentrated ammonia).

DNA synthesis is carried out on a 394 Applied Biosystem DNA Synthesizer using standard phosphoramidite chemistry (Gait et al. *Oligonucleotide Synthesis: A practical Approach:* Oxford University Press: New York, 1990).

The polynucleotide is deprotected upon treatment with concentrated NH₃ for 1 hour at 55° C. The DMTr group is removed upon treatment with 3% Cl₃CCO₂H in DCM (5 min), followed by extensive washing with DCM, THF, MeOH, tris-HCl buffer (20 mM, pH 8, NaCl 160 mM), and dH₂O.

The functionalized polynucleotide thus obtained is further derivatised with dye compounds 4, 900, 1000, 100, 200 or 300 (1–1.5 equivalents) under the following concentration conditions: for 4 μmoles of polynucleotide, HBTU (25 mM), DIEA (100 mM), dye 4, 900, 1000, 100, 200 or 300 (25 mM), DMA (0.5 mL), shake at 20° C. for 2 hours. The resin is washed with DMF, MeOH, DCM and dried under high vacuum. After this step the phosphate backbone, if necessary, is optionally deprotected using a mixture of thiophenol/Et₃N/dioxane (1/½) for 45 min and washed with dioxane and MeOH. The peptide-polynucleotide conjugate is detached from any resin and deprotected on the terminal Fmoc-amino acid group (1 hour in concentrated ammonia at 55° C.) and filtered through 0.8 μm disposable syringe filter (Corning). After this step, the polynucleotide-dye conjugate is deprotected on the nucleobases upon treatment for 18 hours at 45–50° C. The solution is lyophilized and ethanol precipitated 3 times from 3 M AcONa pH 5.2 and used without further purification for enzyme catalyzed peptide coupling.

Alternative coupling methodology of peptides, nucleic acids, and carbohydrates having a free amino group with the activated esters 900, 1000, 100, 200 or 300.

To a stirred solution of the activated ester 900, 1000, 100, 200 or 300 or free acids of compounds 900, 1000, 100, 200 or 300 (1.0 equivalents) in dimethylformamide (0.10 Molar; methylene chloride is also valid) at 25° C., is added the desired protein, peptide, nucleic acid or carbohydrate having a free amino moiety (1.1 equivalents) and 1-hydroxybenzotriazole (HOBT; 1.1 equivalents). Next dicyclohexylcarbodiimide (1.2 equivalents) is optionally added and the reaction is stirred for 14 hours. The mixture is diluted with ether, filtered and the filtrate is washed with aqueous NaHCO₃ (2×), water (2×), and brine (2×). The organic phase is dried over MgSO4 and then concentrated. Purification by flash column chromatography affords the conjugated compound.

While a preferred form of the invention has been shown in the drawings and described, since variations in the preferred form will be apparent to those skilled in the art, the invention should not be construed as limited to the specific form shown and described, but instead is as set forth in the following claims:

What is claimed is:

1. A process for detecting an enzyme within a sample, the enzyme being of a type having a hydrolytic activity with respect to a biomolecule, the process comprising the following steps:

Step A: admixing the sample with a fluorescent conjugate under reaction conditions within an aqueous phase, the fluorescent conjugate including a biomolecule and a fluorescent dye, the biomolecule being hydrolyzable by the enzyme for forming a fluorescent fragment which includes the fluorescent dye and which is solvatochromic and separable from the fluorescent conjugate by transfer from the aqueous phase into an organic phase of a biphasic mixture; then Step B: enzymatically hydrolyzing the fluorescent conjugate within the admixture of said Step A for forming the fluorescent fragment; then Step C: transferring the fluorescent fragment formed in said Step B from the aqueous phase into the organic phase of the biphasic mixture; and then Step D: detecting the fluorescent fragment transferred into the organic phase in said Step C for indicating the presence of the enzyme within the sample;

wherein the fluorescent conjugate is represented by the following structure:

D-L-B wherein:

D- is a fluorescent dye having a radical portion and is represented by the following structure:

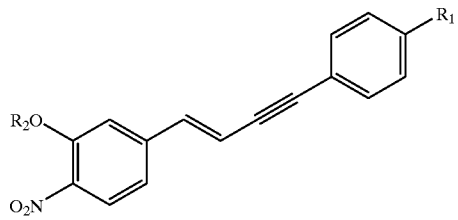

wherein $R_1$ is selected from the group consisting of radicals represented by the following structures:

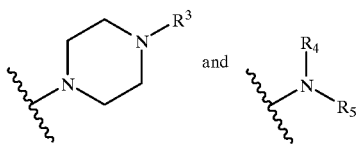

wherein $R_4$ and $R_5$ are independently selected from the group consisting of C1–C6 alkyls and $R_2$ and $R_3$ are independently either hydrogen or absent so as to form a radical;

with a proviso that one of $R_2$ and $R_3$ is absent so as to form the radical of said fluorescent dye;

-L- is a diradical linker selected from a group represented by the following structures:

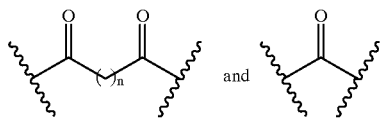

wherein $1 \leq n \leq 4$; and

-B is a biomolecule having a radical portion, wherein the radical portion is selected from a group consisting of hydroxyl radical and amino radical;

wherein said diradical linker -L- links the radical of said fluorescent dye D- to the radical of said biomolecule -B to form said fluorescent conjugate.

2. The process according to claim 1 wherein said biomolecule is selected from a group consisting of carbohydrate, nucleic acid, and peptide.

3. The process according to claim 2 represented by the following structure:

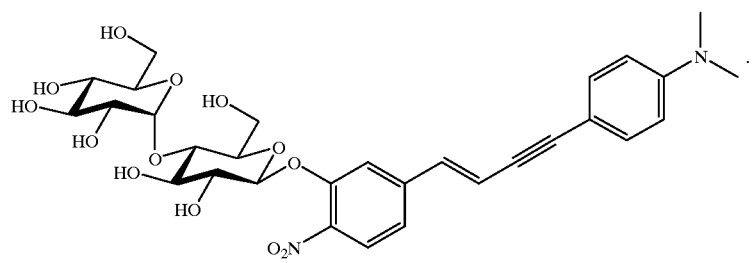

4. The process according to claim 3 represented by the following structure:

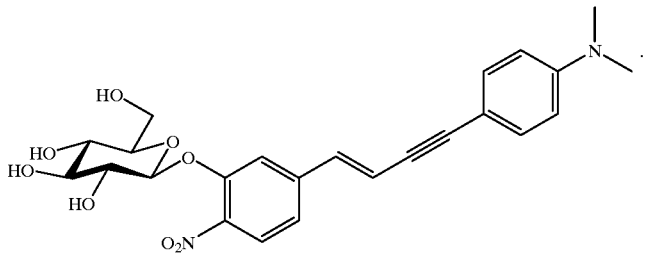

5. The process according to claim 3 wherein the organic phase is an oil and a fluorescence enhancement is achieved by use of a volumetric ratio of the organic phase to the aqueous phase of the biphasic mixture of 1/100 or less.

6. The process according to claim 3 wherein the biomolecule is selected from the group consisting of carbohydrates, nucleic acids, peptides, and phosphoric biomolecules, and the enzyme is selected from the group consisting of glycosidase, alkaline phosphatase, and protease.

7. A process for detecting an enzyme within a sample, the enzyme being of a type having a hydrolytic activity with respect to a biomolecule, the process comprising the following steps:
Step A: admixing the sample with a fluorescent conjugate under reaction conditions within an aqueous phase, the fluorescent conjugate including a biomolecule and a fluorescent dye, the biomolecule being hydrolyzable by the enzyme for forming a fluorescent fragment which includes the fluorescent dye and which is solvatochromic and separable from the fluorescent conjugate by transfer from the aqueous phase into an organic phase of a biphasic mixture; then
Step B: enzymatically hydrolyzing the fluorescent conjugate within the admixture of said Step A for forming the fluorescent fragment; then
Step C: transferring the fluorescent fragment formed in said Step B from the aqueous phase into the organic phase of the biphasic mixture; and then
Step D: detecting the fluorescent fragment transferred into the organic phase in said Step C for indicating the presence of the enzyme within the sample;
wherein the fluorescent conjugate is represented by the following structure:
D-B wherein:
D- is a radical of a fluorescent dye represented by the following structure:

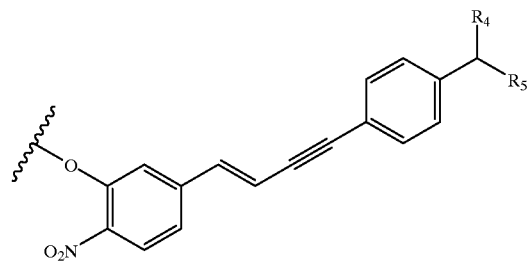

wherein $R_4$ and $R_5$ are independently selected from the group consisting of C1–C6 alkyls; and -B is a biomolecule having a radical portion, wherein the radical portion is selected from a group consisting of hydroxyl radical and amino radical;
wherein
the radical of said fluorescent dye D- is linked to the radical portion of said biomolecule -B to form said fluorescent conjugate.

8. The process according to claim 7 wherein said biomolecule is selected from a group consisting of carbohydrate, nucleic acid, and peptide.

9. The process according to claim 8 wherein the organic phase is an oil and a fluorescence enhancement is achieved by use of a volumetric ratio of the organic phase to the aqueous phase of the biphasic mixture of 1/100 or less.

10. The process according to claim 8 wherein the biomolecule is selected from the group consisting of carbohydrates, nucleic acids, peptides, and phosphoric biomolecules, and the enzyme is selected from the group consisting of glycosidase, alkaline phosphatase, and protease.

11. A process for detecting an enzyme within a sample, the enzyme being of a type having a hydrolytic activity with respect to a biomolecule, the process comprising the following steps:
Step A: admixing the sample with a fluorescent conjugate under reaction conditions within an aqueous phase, the fluorescent conjugate including a biomolecule and a fluorescent dye, the biomolecule being hydrolyzable by the enzyme for forming a fluorescent fragment which includes the fluorescent dye and which is solvatochromic and separable from the fluorescent conjugate by transfer from the aqueous phase into an organic phase of a biphasic mixture; then
Step B: enzymatically hydrolyzing the fluorescent conjugate within the admixture of said Step A for forming the fluorescent fragment; then
Step C: transferring the fluorescent fragment formed in said Step B from the aqueous phase into the organic phase of the biphasic mixture; and then
Step D: detecting the fluorescent fragment transferred into the organic phase in said Step C for indicating the presence of the enzyme within the sample;
wherein the fluorescent conjugate is represented by the following structure:
$B_1$-L-D-L-$B_2$ wherein:
D- is a fluorescent dye having two radicals portions and is represented by the following structure:

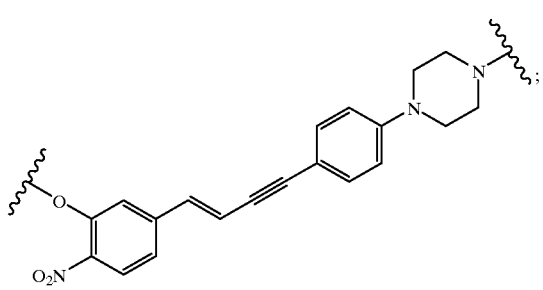

-L- is a diradical linker selected from a group represented by the following structures:

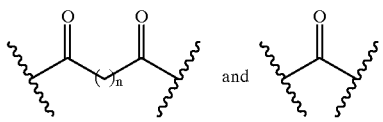

$1 \leq n \leq 4$; and $B_1$- and $-B_2$ are independently selected from a group of biomolecules, each biomolecule having a radical portion, wherein the radical portion is selected from a group consisting of hydroxyl radical and amino radical; wherein said diradical linker -L- links each of the radicals of said fluorescent dye D- to the radical of each of said biomolecules $B_1$- and $-B_2$ to form said fluorescent conjugate.

12. The process according to claim 11 wherein each of said biomolecules $B_1$- and $-B_2$ are independently selected from a group consisting of carbohydrate, nucleic acid, and peptide.

13. The process according to claim 12 wherein the organic phase is an oil and a fluorescence enhancement is achieved by use of a volumetric ratio of the organic phase to the aqueous phase of the biphasic mixture of 1/100 or less.

14. A process according to claim 12 wherein the biomolecule is selected from the group consisting of carbohydrates, nucleic acids, peptides, and phosphoric biomolecules, and the enzyme is selected from the group consisting of glycosidase, alkaline phosphatase, and protease.

15. A process for detecting an enzyme within a sample, the enzyme being of a type having a hydrolytic activity with respect to a biomolecule, the process comprising the following steps:

Step A: admixing the sample with a fluorescent conjugate under reaction conditions within an aqueous phase, the fluorescent conjugate including a biomolecule and a fluorescent dye, the biomolecule being hydrolyzable by the enzyme for forming a fluorescent fragment which includes the fluorescent dye and which is solvatochromic and separable from the fluorescent conjugate by transfer from the aqueous phase into an organic phase of a biphasic mixture; then Step B: enzymatically hydrolyzing the fluorescent conjugate within the admixture of said Step A for forming the fluorescent fragment; then Step C: transferring the fluorescent fragment formed in said Step B from the aqueous phase into the organic phase of the biphasic mixture; and then Step D: detecting the fluorescent fragment transferred into the organic phase in said Step C for indicating the presence of the enzyme within the sample;

wherein the fluorescent conjugate is represented by the following structure:

$B_1$-D-L-$B_2$ wherein:

D- is a fluorescent dye having a hydroxyl radical and an amino radical and is represented by the following structure:

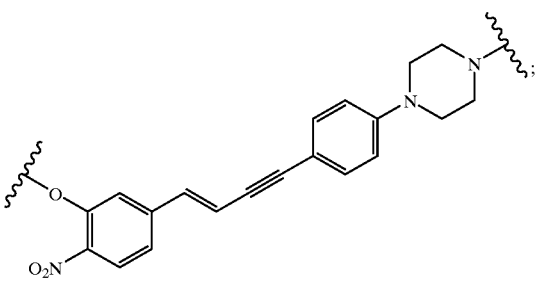

-L- is a diradical linker selected from a group represented by the following structures:

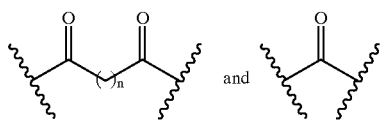

wherein $1 \leq n \leq 4$; and $B_1$- and $-B_2$ are independently selected from a group of biomolecules, each biomolecule having a radical portion, wherein the radical portion is selected from a group consisting of hydroxyl radical and amino radical; wherein said diradical linker -L- links the amino radical of said fluorescent dye D- to the radical of said biomolecule $-B_2$ and the hydroxyl radical of said fluorescent dye D- is linked directed to the radical of said biomolecule $-B_1$.

16. The process according to claim 15 wherein each of said biomolecules $B_1$- and $-B_2$ are independently selected from a group consisting of carbohydrate, nucleic acid, and peptide.

17. The process according to claim 16 wherein the organic phase is an oil and a fluorescence enhancement is achieved by use of a volumetric ratio of the organic phase to the aqueous phase of the biphasic mixture of 1/100 or less.

18. The process according to claim 16 wherein the biomolecule is selected from the group consisting of carbohydrates, nucleic acids, peptides, and phosphoric biomolecules, and the enzyme is selected from the group consisting of glycosidase, alkaline phosphatase, and protease.

19. A process for detecting an enzyme within a sample, the enzyme being of a type having a hydrolytic activity with respect to a biomolecule, the process comprising the following steps:

Step A: admixing the sample with a fluorescent conjugate under reaction conditions within an aqueous phase, the fluorescent conjugate including a biomolecule and a fluorescent dye, the biomolecule being hydrolyzable by the enzyme for forming a fluorescent fragment which includes the fluorescent dye and which is solvatochromic and separable from the fluorescent conjugate by transfer from the aqueous phase into an organic phase of a biphasic mixture; then Step B: enzymatically hydrolyzing the fluorescent conjugate within the admixture of said Step A for forming the fluorescent fragment; then Step C: transferring the fluorescent fragment formed in said Step B from the aqueous phase into the organic phase of the biphasic mixture; and then Step D: detecting the fluorescent fragment transferred into the organic phase in said Step C for indicating the presence of the enzyme within the sample;

wherein the fluorescent conjugate is represented by the following structure:

$D_1$-$L_1$-B-$L_2$-$D_2$ wherein:

$D_1$ and $D_2$ are each a fluorescent dye having a radical portion and are each independently represented by the following structure:

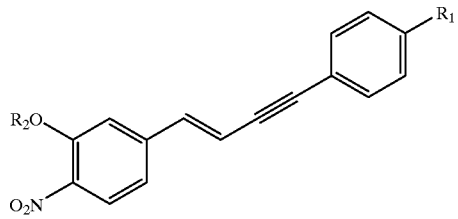

wherein $R_1$ is independently selected from the group consisting of radicals represented by the following structures:

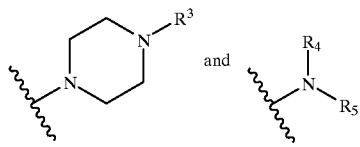

wherein $R_4$ and $R_5$ are independently selected from the group consisting of C1–C6 alkyls and $R_2$ and $R_3$ are independently either hydrogen or absent so as to form a radical;

with a proviso that, within each of said $D_1$ and $D_2$, one of $R_2$ and $R_3$ is absent so as to form the radical of said fluorescent dye;

$L_1$ and $L_2$ are each diradical linkers independently selected from a group represented by the following structures:

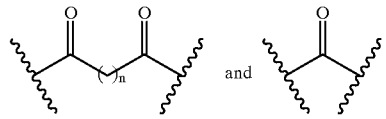

wherein $1 \leq n \leq 4$; and

-B is selected from a group of biomolecules, each biomolecule having a first and a second radical portion, wherein the first and second radical portions are independently selected from a group consisting of hydroxyl radical and amino radical;

wherein
said fluorescent dye $D_1$ is linked to the first radical of said biomolecule by said diradical linker -L-; and
said fluorescent dye $D_2$ is linked to the second radical of said biomolecule by said diradical linker -L- to form said fluorescent conjugate.

20. The process according to claim 19 wherein said biomolecule B- is selected from a group consisting of carbohydrate, nucleic acid, and peptide.

21. The process according to claim 20 wherein the organic phase is an oil and a fluorescence enhancement is achieved by use of a volumetric ratio of the organic phase to the aqueous phase of the biphasic mixture of 1/100 or less.

22. The process according to claim 20 wherein the biomolecule is selected from the group consisting of carbohydrates, nucleic acids, peptides, and phosphoric biomolecules, and the enzyme is selected from the group consisting of glycosidase, alkaline phosphatase, and protease.

23. A process for detecting an enzyme within a sample, the enzyme being of a type having a hydrolytic activity with respect to a biomolecule, the process comprising the following steps:

Step A: admixing the sample with a fluorescent conjugate under reaction conditions within an aqueous phase, the fluorescent conjugate including a biomolecule and a fluorescent dye, the biomolecule being hydrolyzable by the enzyme for forming a fluorescent fragment which includes the fluorescent dye and which is solvatochromic and separable from the fluorescent conjugate by transfer from the aqueous phase into an organic phase of a biphasic mixture; then Step B: enzymatically hydrolyzing the fluorescent conjugate within the admixture of said Step A for forming the fluorescent fragment; then Step C: transferring the fluorescent fragment formed in said Step B from the aqueous phase into the organic phase of the biphasic mixture; and then Step D: detecting the fluorescent fragment transferred into the organic phase in said Step C for indicating the presence of the enzyme within the sample;

wherein the fluorescent conjugate is represented by the following structure:

$D_1$-B-$L_2$-$D_2$ wherein:

$D_1$ is a radical of a fluorescent dye represented by the following structure:

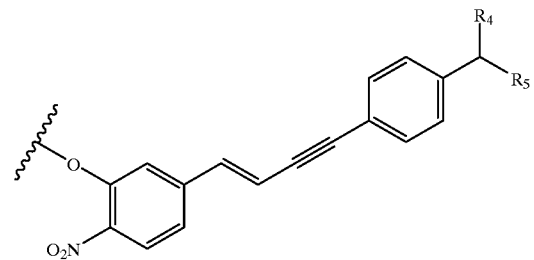

wherein $R_4$ and $R_5$ are independently selected from the group consisting of C1–C6 alkyls;

$D_2$ is a fluorescent dye having a radical portion represented by the following structure:

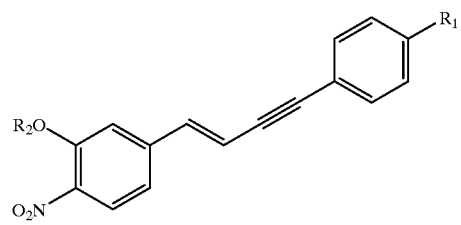

wherein R₁ is independently selected from the group consisting of radicals represented by the following structures:

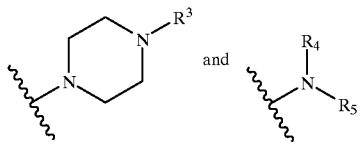

wherein R₂ and R₃ are independently either hydrogen or absent so as to form a radical;
with a proviso that, within each of said $D_1$ and $D_2$, one of R₂ and R₃ is absent so as to form the radical of said fluorescent dye;
L is a diradical linker selected from a group represented by the following structures:

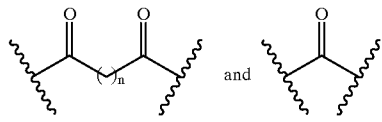

wherein $1 \leq n \leq 4$; and

-B is selected from a group of biomolecules, each biomolecule having a first and a second radical portion, wherein the first and second radical portions are independently selected from a group consisting of hydroxyl radical and amino radical;
wherein
said fluorescent dye $D_1$ is linked directly to the first radical of said biomolecule; and
said fluorescent dye $D_2$ is linked to the second radical of said biomolecule by said diradical linker -L- to form said fluorescent conjugate.

24. The process according to claim 23 wherein said biomolecule B- is selected from a group consisting of carbohydrate, nucleic acid, and peptide.

25. The process according to claim 24 wherein the organic phase is an oil and a fluorescence enhancement is achieved by use of a volumetric ratio of the organic phase to the aqueous phase of the biphasic mixture of 1/100 or less.

26. A process according to claim 24 wherein the biomolecule is selected from the group consisting of carbohydrates, nucleic acids, peptides, and phosphoric biomolecules, and the enzyme is selected from the group consisting of glycosidase, alkaline phosphatase, and protease.

* * * * *